(12) United States Patent
Kim et al.

(10) Patent No.: US 9,490,435 B2
(45) Date of Patent: Nov. 8, 2016

(54) IRIDIUM COMPLEX AND ORGANIC LIGHT-EMITTING DEVICE INCLUDING THE SAME

(71) Applicants: Samsung Display Co., LTD., Yongin, Gyeonggi-do (KR); Pusan National University Industry-University Coorperation Foundation, Busan (KR)

(72) Inventors: Soung-Wook Kim, Yongin (KR); Jae-Hong Kim, Yongin (KR); Myeong-Suk Kim, Yongin (KR); Moon-Jae Lee, Yongin (KR); Sung-Ho Jin, Busan (KR)

(73) Assignees: SAMSUNG DISPLAY CO., LTD, Yongin-Si (KR); PUSAN NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 461 days.

(21) Appl. No.: 14/056,935

(22) Filed: Oct. 17, 2013

(65) Prior Publication Data
US 2014/0367647 A1    Dec. 18, 2014

(30) Foreign Application Priority Data
Jun. 12, 2013 (KR) .................. 10-2013-0067327

(51) Int. Cl.
| | | |
|---|---|---|
| H01L 51/00 | (2006.01) | |
| C07F 15/00 | (2006.01) | |
| C09K 11/06 | (2006.01) | |
| H01L 51/50 | (2006.01) | |

(52) U.S. Cl.
CPC ....... H01L 51/0085 (2013.01); C07F 15/0033 (2013.01); C09K 11/06 (2013.01); C09K 2211/185 (2013.01); H01L 51/5016 (2013.01)

(58) Field of Classification Search
None
See application file for complete search history.

(56) References Cited

U.S. PATENT DOCUMENTS

| | | | |
|---|---|---|---|
| 2005/0008895 | A1 | 1/2005 | Takada et al. |
| 2005/0031903 | A1 | 2/2005 | Park et al. |
| 2011/0282059 | A1 | 11/2011 | Baranoff et al. |

FOREIGN PATENT DOCUMENTS

| | | |
|---|---|---|
| KR | 10-2004-0106236 A | 12/2004 |
| KR | 10-2005-0082059 A | 8/2005 |
| KR | 10-2011-0131200 A | 12/2011 |
| KR | 10-2012-0135837 A | 12/2012 |

*Primary Examiner* — J. L. Yang
(74) *Attorney, Agent, or Firm* — Lewis Roca Rothgerber Christie LLP

(57) ABSTRACT

Provided are an iridium complex represented by Formula 1 below and an organic light-emitting device including the same.

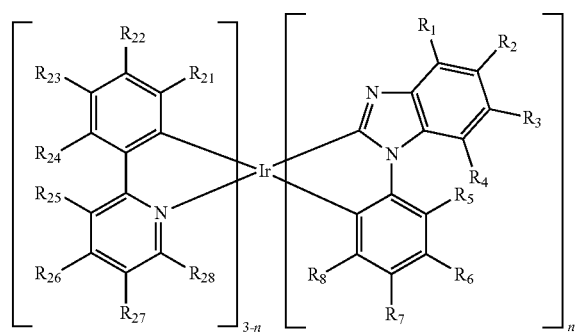

Formula 1

Descriptions of substituents of Formula 1 are the same as described in the detailed description of the present specification.

20 Claims, 2 Drawing Sheets

IRIDIUM COMPLEX AND ORGANIC LIGHT-EMITTING DEVICE INCLUDING THE SAME

CROSS-REFERENCE TO RELATED APPLICATION

This application claims the benefit of Korean Patent Application No. 10-2013-0067327, filed on Jun. 12, 2013, in the Korean Intellectual Property Office, the disclosure of which is incorporated herein in its entirety by reference.

BACKGROUND

1. Field

One or more embodiments of the present invention relate to an iridium complex and an organic light-emitting device including the same.

2. Description of the Related Art

Organic light-emitting devices (OLEDs), which are self-emitting devices, have advantages such as wide viewing angles, high contrast, quick response, high brightness, low driving voltage characteristics, and provide full color images.

A typical OLED has a structure including a substrate, and an anode, a hole transport layer, an emission layer, an electron transport layer, and a cathode which are sequentially stacked on the substrate. The hole transport layer, the emission layer, and the electron transport layer are organic thin films formed of organic compounds.

A driving principle of an organic light-emitting device having such structure is described below.

When a voltage is applied between the anode and the cathode, holes injected from the anode pass the hole transport layer and migrate toward the emission layer, and electrons injected from the cathode pass the electron transport layer and migrate toward the emission layer. The holes and the electrons are recombined with each other in the emission layer to generate excitons. Then, the excitons are transitioned from an excited state to a ground state, thereby generating light.

SUMMARY

One or more aspects of embodiments of the present invention provide for a novel phosphorescent iridium (Ir) complex and an organic light-emitting device having high efficiency, low voltage, high brightness, and long lifespan due to the inclusion of the novel phosphorescent iridium (Ir) complex.

Additional aspects will be set forth in part in the description which follows and, in part, will be apparent from the description, or may be learned by practice of the presented embodiments.

Embodiments of the present invention provide for an iridium complex represented by Formula 1 below.

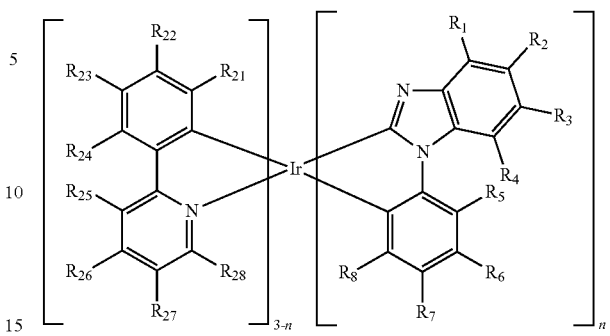

Formula 1

In Formula 1, $R_1$ to $R_8$ and $R_{21}$ to $R_{28}$ may be each independently selected from a hydrogen atom, a deuterium atom, a halogen, a hydroxyl group, a cyano group, a nitro group, an amino group, an amidino group, a hydrazine, a hydrazone, a carboxyl group or salt thereof, a sulfonic acid group or salt thereof, a phosphoric acid group or salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted alkoxy group, a substituted or unsubstituted $C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, and —N($Q_1$)($Q_2$) (wherein, $Q_1$ and $Q_2$ are each independently a hydrogen atom, a substituted or unsubstituted $C_1$-$C_{60}$ alkyl group, a substituted or unsubstituted $C_6$-$C_{30}$ aryl group, or a substituted or unsubstituted $C_2$-$C_{30}$ heteroaryl group);

n is 1 or 2, and

Two or more substituents of $R_5$ to $R_8$ may optionally bind to each other to form a ring.

According to another embodiment of the present invention, an organic light-emitting device includes: a substrate; a first electrode; a second electrode facing the first electrode; and an emission layer between the first electrode and the second electrode, the emission layer including the iridium complex.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
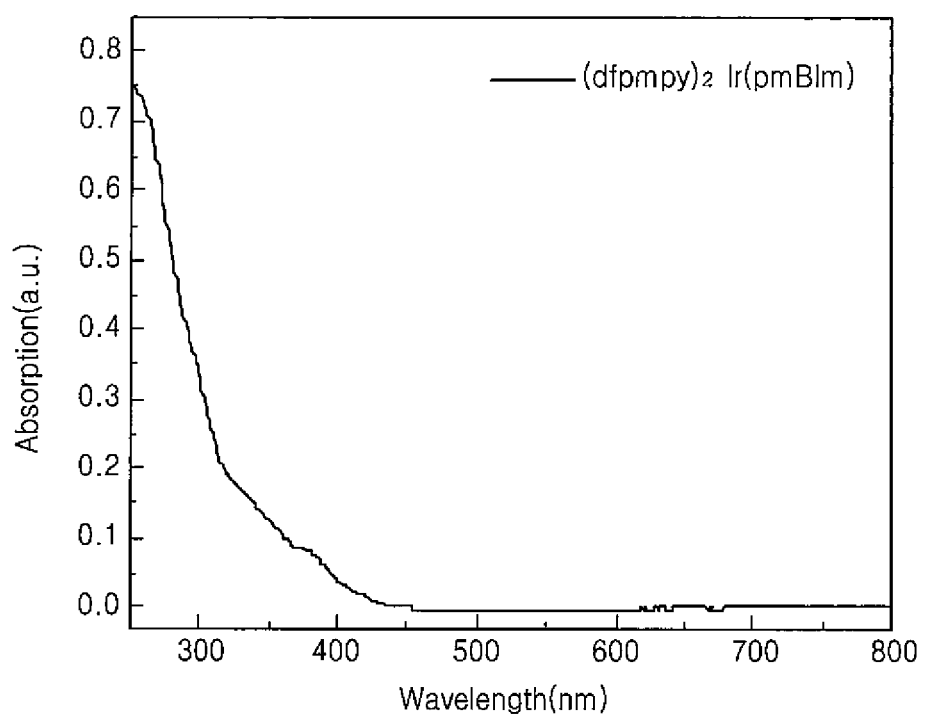
FIG. 1 is an ultraviolet (UV) absorption spectrum of Complex 1 in solution.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list. Further, the use of "may" when describing embodiments of the present invention refers to "one or more embodiments of the present invention."

It will be understood that when an element such as a layer, film, region, or substrate is referred to as being "on" another element, it can be directly on the other element or intervening elements may also be present. In contrast, when an element is referred to as being "directly on" another element, there are no intervening elements present.

An iridium complex according to an embodiment of the present invention is represented by Formula 1 below:

Since from among the two N atoms of the benzoimidazole moiety, only one N atom is substituted with a phenyl group, the effect of the auxiliary ligand on a central metal Ir may differ from when both N atoms of the auxiliary ligand are substituted. The foregoing differences may bring about positive effects on luminescent characteristics and efficiency of the compound according to embodiments of the present invention.

According to some embodiments of the present invention, $R_6$ may be a hydrogen atom, a deuterium atom, a halogen group, a hydroxyl group, a cyano group, a nitro group, or a halogen-substituted $C_1$-$C_{60}$ alkyl group.

According to some embodiments of the present invention, $R_1$ to $R_4$, $R_5$, $R_7$, and $R_8$ may be each independently a hydrogen atom or a deuterium atom.

According to some embodiments of the present invention, two or more substituents of $R_5$ to $R_8$ of Formula 1 may optionally bind to form a ring, to prepare a compound represented by Formula 2:

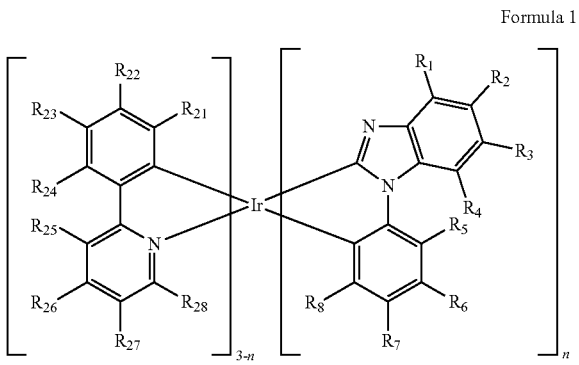

Formula 1

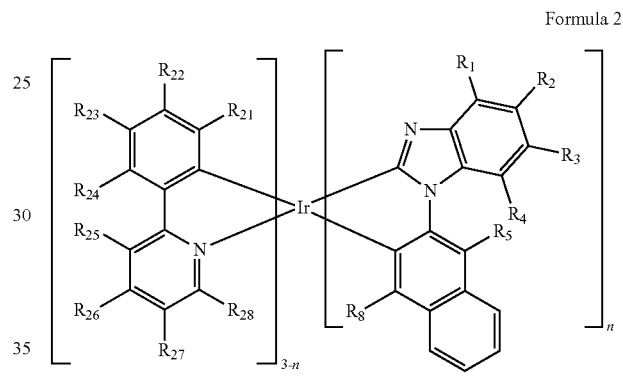

Formula 2

In Formula 1 $R_1$ to $R_8$ and $R_{21}$ to $R_{28}$ may be each independently selected from a hydrogen atom, a deuterium atom, a halogen, a hydroxyl group, a cyano group, a nitro group, an amino group, an amidino group, a hydrazine, a hydrazone, a carboxyl group or salt thereof, a sulfonic acid group or salt thereof, a phosphoric acid group or salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, and —N($Q_1$)($Q_2$) (wherein, $Q_1$ and $Q_2$ are each independently a hydrogen atom, a substituted or unsubstituted $C_1$-$C_{60}$ alkyl group, a substituted or unsubstituted $C_6$-$C_{30}$ aryl group, or a substituted or unsubstituted $C_2$-$C_{30}$ heteroaryl group);

n is 1 or 2, and

Two or more substituents of $R_5$ to $R_8$ may optionally bind to each other to form a ring.

In Formula 1, in a benzoimidazole moiety of an auxiliary ligand, one nitrogen (N) atom binds to (e.g. is bonded to) a phenyl group, and a non-covalent electron pair (e.g. lone pair) of the other N is parallel to the plane of benzoimidazole.

Substituents and n of Formula 2 are the same as defined above in connection with Formula 1.

According to one embodiment of the present invention, $R_{22}$ and $R_{24}$ may be a halogen group, such as —F, —Cl, or —Br.

According to another embodiment of the present invention, $R_{23}$ and $R_{26}$ may be each independently selected from a hydrogen atom, a deuterium atom, a nitro group, a cyano group, a halogen-substituted $C_1$-$C_{60}$ alkyl group, an unsubstituted $C_1$-$C_{60}$ alkyl group, and N($Q_1$)($Q_2$) (wherein, $Q_1$ to $Q_6$ are each independently, a hydrogen atom, a substituted or unsubstituted $C_1$-$C_{60}$ alkyl group, a substituted or unsubstituted $C_6$-$C_{30}$ aryl group, or a substituted or unsubstituted $C_2$-$C_{30}$ heteroaryl group).

According to some embodiments of the present invention, $R_{21}$, $R_{25}$, $R_{27}$, and $R_{28}$ may be each independently a hydrogen atom or a deuterium atom.

Hereinafter, definitions of representative substituents from among substituents used herein will be presented (the number of carbon numbers restricting a substituent is not limited, and does not limit the properties of the substituent, and unless defined otherwise, the definition of the substituent is consistent with a general definition thereof).

The unsubstituted $C_1$ to $C_{60}$ alkyl group used herein may refer to a linear or branched alkyl group, and non-limiting examples thereof are a methyl group, an ethyl group, a propyl group, an isobutyl group, a sec-butyl group, a pentyl group, an iso-amyl group, a hexyl group, a heptyl group, an octyl group, a nonanyl group, and a dodecyl group. The substituted $C_1$-$C_{60}$ alkyl group may refer to the unsubstituted $C_1$-$C_{60}$ alkyl group in which and at least one hydrogen atom is substituted with a deuterium atom, a halogen atom, a hydroxyl group, a nitro group, a cyano group, an amino group, an amidino group, a hydrazine, a hydrazone, a carboxyl group or salt thereof, a sulfonic acid or salt thereof, a phosphoric acid or salt thereof, a $C_1$ to $C_{10}$ alkyl group, a $C_1$ to $C_{10}$ alkoxy group, a $C_2$ to $C_{10}$ alkenyl group, a $C_2$ to $C_{10}$ alkynyl group, a $C_6$ to $C_{16}$ aryl group, or a $C_2$ to $C_{16}$ heteroaryl group.

The unsubstituted $C_2$ to $C_{60}$ alkenyl group used herein may refer to a hydrocarbon chain having at least one carbon-carbon double bond at one or more positions along a carbon chain of the unsubstituted $C_2$-$C_{60}$ alkyl group. For example, the unsubstituted $C_2$ to $C_{60}$ alkenyl group may include a terminal alkene and/or an internal alkene. Non-limiting examples thereof include ethenyl, prophenyl, and butenyl. The substituted $C_2$ to $C_{60}$ alkenyl group may refer to the unsubstituted $C_2$ to $C_{60}$ alkenyl group in which at least one hydrogen atom is substituted with the same substituents as described in connection with the substituted alkyl group.

The unsubstituted $C_2$ to $C_{60}$ alkynyl group used herein may refer to a hydrocarbon chain having at least one carbon-carbon triple bond at one or more positions along a carbon chain of the unsubstituted $C_2$-$C_{60}$ alkyl group. For example, the unsubstituted $C_2$ to $C_{60}$ alkynyl group may include a terminal alkyne and/or an internal alkyne. Non-limiting examples thereof include acetylene, propylene, phenylacetylene, naphthylacetylene, isopropylacetylene, t-butylacetylene, and diphenylacetylene. The substituted $C_2$ to $C_{60}$ alkynyl group may refer to the unsubstituted $C_2$ to $C_{60}$ alkynyl group in which at least one hydrogen atom is substituted with the same substituents as described in connection with the substituted alkyl group.

The unsubstituted $C_3$ to $C_{60}$ cycloalkyl group used herein refers to a $C_3$ to $C_{60}$ cyclic alkyl group. The substituted $C_3$ to $C_{60}$ cycloalkyl group may refer to the unsubstituted $C_3$ to $C_{60}$ cycloalkyl group in which at least one hydrogen atom is substituted with the same substituents as described in connection with the substituted alkyl group.

The unsubstituted $C_1$ to $C_{60}$ alkoxy group used herein may refer to a group having —OA (wherein A is the unsubstituted $C_1$ to $C_{60}$ alkyl group), and non-limiting examples thereof include ethoxy, ethoxy, isopropyloxy, butoxy, and pentoxy. The substituted $C_1$ to $C_{60}$ alkoxy group may refer to the unsubstituted $C_1$ to $C_{60}$ alkoxy group in which at least one hydrogen atom is substituted with the same substituents as described in connection with the substituted alkyl group.

The unsubstituted $C_6$ to $C_{60}$ aryl group used herein may refer to a carbocyclic aromatic system having at least one aromatic ring, and when the number of rings is two or more, the rings may be fused to each other or may be linked to each other via, for example, a single bond. The term 'aryl' includes an aromatic system, such as phenyl, naphthyl, or anthracenyl. The substituted $C_6$ to $C_{60}$ aryl group may refer to the unsubstituted $C_6$ to $C_{60}$ aryl group in which at least one hydrogen atom is substituted with the same substituents as described in connection with the substituted alkyl group.

Non-limiting examples of the substituted or unsubstituted $C_6$ to $C_{60}$ aryl group include a phenyl group, a $C_1$ to $C_{10}$ alkylphenyl group (for example, an ethylphenyl group), a biphenyl group, a $C_1$ to $C_{10}$ alkylbiphenyl group, a $C_1$ to $C_{60}$ akoxybiphenyl group, o-, m-, or p-tolyl groups, o-, m- or p-cumenyl groups, a mesityl group, a phenoxyphenyl group, a (α,α-dimethylbenzene)phenyl group, a (N,N'-dimethyl) aminophenyl group, a (N,N'-diphenyl)aminophenyl group, a pentalenyl group, an indenyl group, a naphthyl group, a $C_1$ to $C_{10}$ alkylnaphthyl group (for example, methylnaphthyl group), a $C_1$ to $C_{10}$ akoxynaphthyl group (for example, methoxynaphthyl group), n anthracenyl group, an azrenyl group, a heptalenyl group, an acenaphthylenyl group, a phenalenyl group, a fluorenyl group, an anthraquinolinyl group, a methylan anthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentasenyl group, a tetraphenylenyl group, a hexaphenyl group, a hexacenyl group, a rubicenyl group, a coroneryl group, trinaphthylenyl group, a heptaphenyl group, a heptacenyl group, a piranthrenyl group, and an obarenyl group.

The unsubstituted $C_1$-$C_{60}$ heteroaryl group used herein may refer to the unsubstituted aryl group with at least one hetero atom selected from nitrogen (N), oxygen (O), phosphorous (P), and sulfur (S) as ring atoms, and when the group has two or more rings, the rings may be fused to each other or may be linked to each other via, for example, a single bond. Non-limiting examples of the unsubstituted $C_1$-$C_{60}$ heteroaryl group are a pyrazolyl group, an imidazolyl group, a oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, and a dibenzothiophene group. The substituted $C_1$-$C_{60}$ heteroaryl group may refer to the unsubstituted $C_1$-$C_{60}$ heteroaryl group in which at least one hydrogen atom is substituted with the same substituents described in connection with the substituted alkyl group.

The unsubstituted $C_6$ to $C_{60}$ aryloxy group used herein may refer to a group represented by —$OA_1$, wherein $A_1$ is the $C_6$ to $C_{60}$ aryl group. A non-limiting example of the aryloxy group is a phenoxy group. The substituted $C_6$ to $C_{60}$ aryloxy group may refer to the unsubstituted $C_6$ to $C_{60}$ aryloxy group in which at least one hydrogen atom is substituted with the same substituents as described in connection with the substituted alkyl group.

The unsubstituted $C_6$ to $C_{60}$ arylthio group used herein may refer to a group represented by —$SA_1$, wherein $A_1$ is the $C_6$ to $C_{60}$ aryl group. Non-limiting examples of the arylthio group include a benzenethio group and a naphthylthio group. The substituted $C_6$ to $C_{60}$ arylthio group may refer to the unsubstituted $C_6$ to $C_{60}$ arylthio group in which at least one hydrogen atom is substituted with the same substituents described in connection with the substituted alkyl group.

The unsubstituted $C_6$ to $C_{60}$ condensed polycyclic group used herein may refer to i) substituents including two or more rings in which at least one aromatic ring and at least one non-aromatic ring are fused to each other or ii) substituents including unsaturated groups in the ring but incapable of forming a conjugated structure. Thus, the unsubstituted $C_6$ to $C_{60}$ condensed polycyclic group is distinct from the aryl group or the heteroaryl group as it has a non-aromatic component. The substituted $C_6$ to $C_{60}$ condensed polycyclic group may refer to the unsubstituted $C_6$ to $C_{60}$ condensed polycyclic group in which at least one hydrogen atom is substituted with one of those substituents described above in conjunction with the substituted alkyl group.

Examples of the iridium complex represented by Formula 1 are Compounds 1-18 below, but are not limited thereto.

1
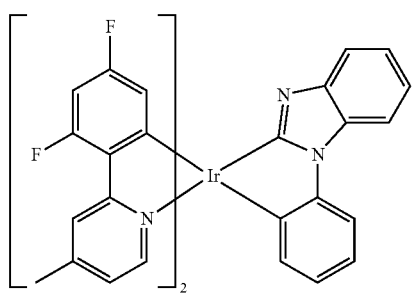
2
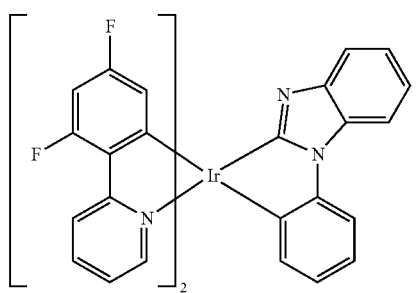
3
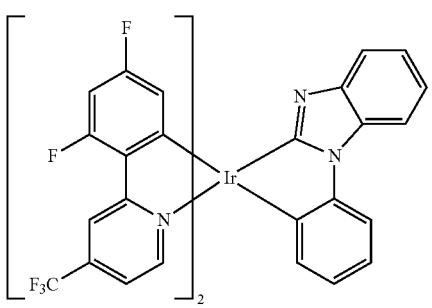
4
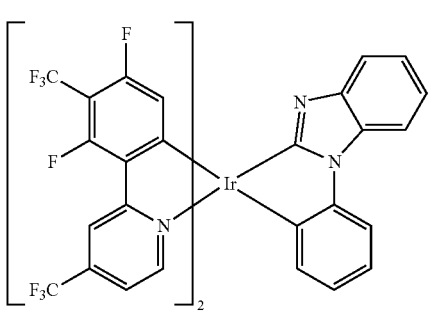
5
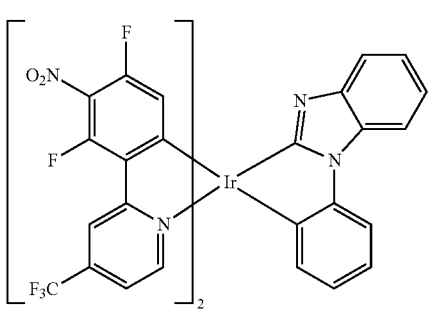
6
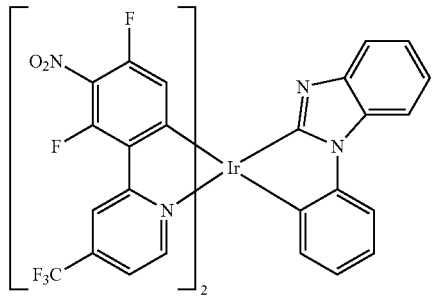
7
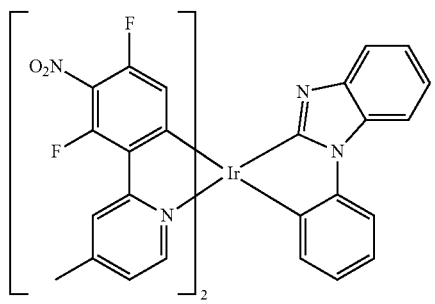
8
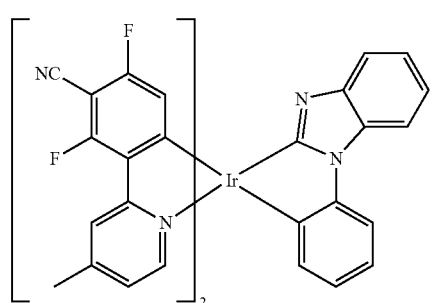
9
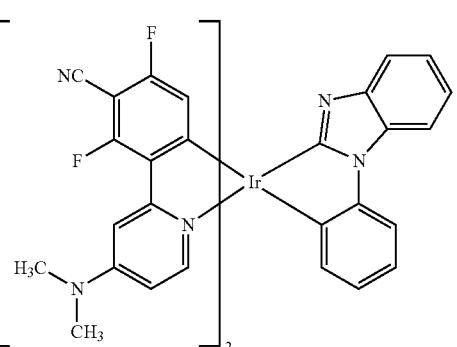
10
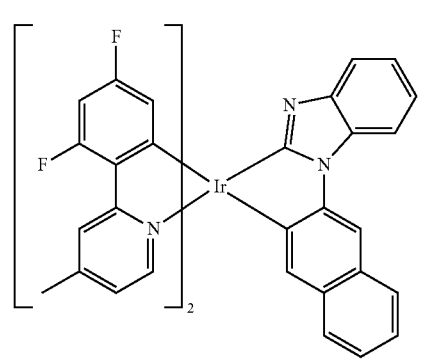

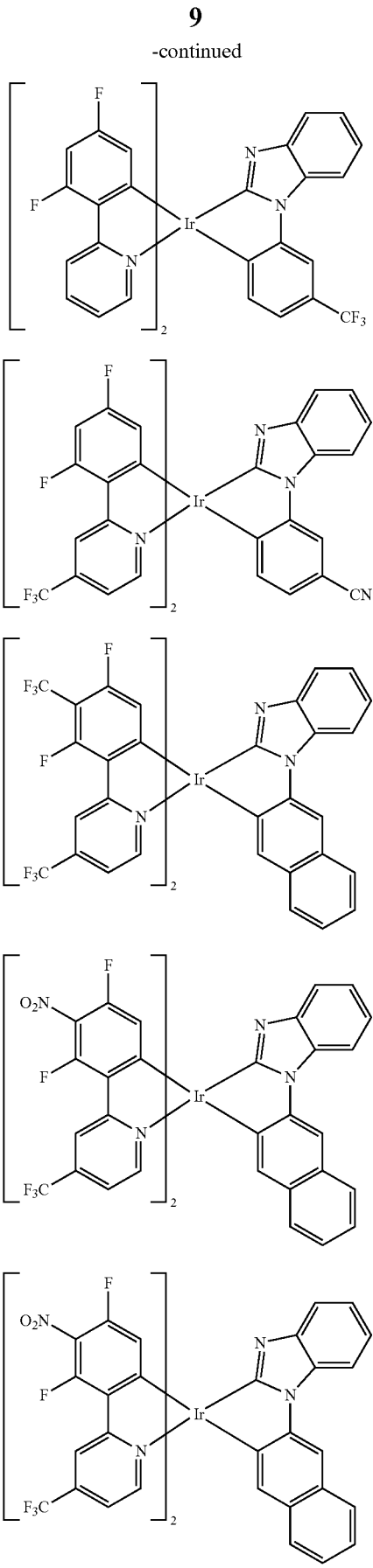
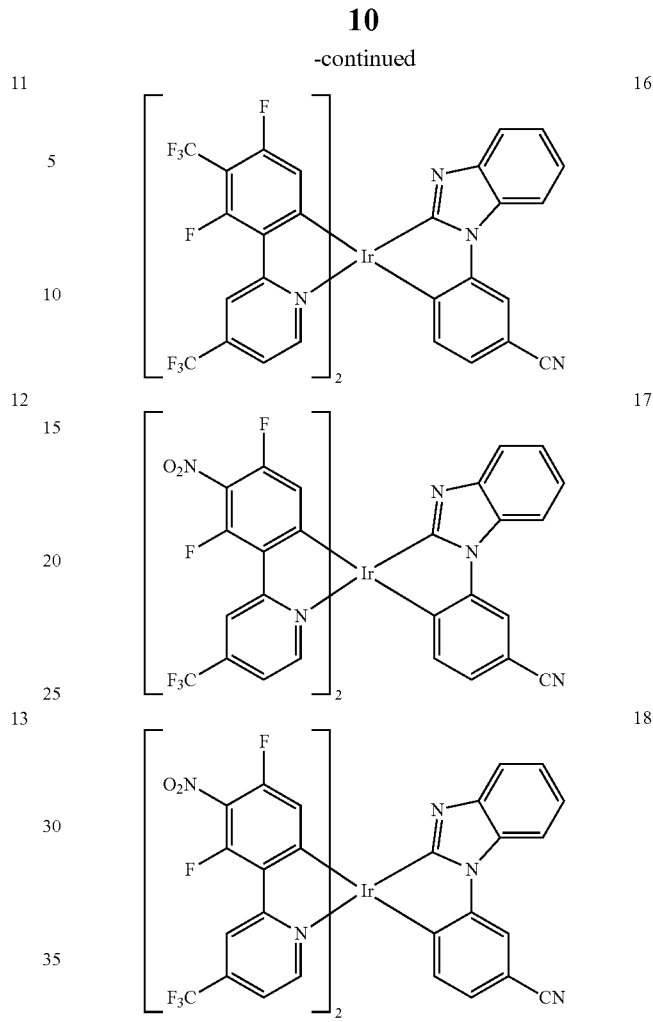

At least one of the iridium complex represented by Formula 1 may be used between a pair of electrodes of an organic light-emitting device. For example, at least one of the iridium complex may be used in an emission layer.

Embodiments of the present invention provide an organic light-emitting device including: a first electrode; a second electrode facing the first electrode; and an organic layer between the first electrode and the second electrode, the organic layer including an emission layer, and at least one of the iridium complex represented by Formula 1.

The wording that "(an organic layer) includes at least one iridium complex" used herein should be understood as "(an organic layer) may include one iridium complex represented by Formula 1 or two or more of iridium complexes represented by Formula 1".

For example, the organic layer may include only Complex 1 as the iridium complex. In this regard, Complex 1 may exist in an emission layer of the organic light-emitting device. According to another embodiment, the organic layer may include Complex 1 and Complex 2 as the iridium complex. In this regard, Complex 1 and Complex 2 may exist in the same layer (for example, emission layer).

The organic layer may include at least one layer selected from a hole injection layer, a hole transport layer, a functional layer having a hole injection function and a hole transport function (hereinafter referred to as "H-functional layer"), a buffer layer, and an electron blocking layer, and the organic layer may further include a hole blocking layer, an electron transport layer, and an electron injection layer.

The term "organic layer" used herein refers to a single layer and/or a plurality of layers disposed between a first electrode and a second electrode of an organic light-emitting device.

In some embodiments, the organic layer includes an emission layer, and the emission layer, in turn, includes at least one iridium complex represented by Formula 1.

The iridium complex included in the emission layer may act as a phosphorescent dopant, and the emission layer may further include a host. The host will be described later.

An organic light-emitting device including the iridium complex of Formula 1 may emit green light and blue light, and in some embodiments, may emit blue phosphorescent light.

Figure 3:
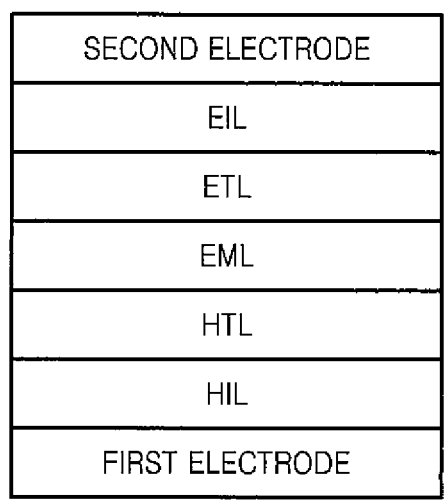
FIG. 3 is a schematic view of the structure of an organic light-emitting device according to an embodiment of the present invention.

FIG. 3 is a schematic cross-sectional view of an organic light-emitting device according to an embodiment of the present invention. Hereinafter, with reference to FIG. 3, the structure of an organic light-emitting device according to an embodiment of the present invention, and a method of manufacturing the organic light-emitting device, according to an embodiment of the present invention, will be described in detail.

A substrate (not shown) may be any one of various substrates suitable for use in an organic light-emitting device, and may be a glass substrate or a transparent plastic substrate with excellent mechanical strength, thermal stability, transparency, surface smoothness, ease of handling, and water repellency.

A first electrode may be formed by, for example, depositing or sputtering a material for the first electrode on the substrate. When the first electrode is an anode, the material for the first electrode may be selected from materials with a high work function to make holes be easily injected. The first electrode may be a reflective electrode or a transmissive electrode. The material for the first electrode may be a transparent material with high conductivity, and non-limiting examples of such a material are indium tin oxide (ITO), indium zinc oxide (IZO), tin oxide ($SnO_2$), and zinc oxide (ZnO). When magnesium (Mg), aluminum (Al), aluminum-lithium (Al—Li), calcium (Ca), magnesium-indium (Mg—In), magnesium-silver (Mg—Ag), or the like is used, the first electrode may be a reflective electrode.

The first electrode may have a single- or multi-layered structure. For example, the first electrode may have a three-layered structure of ITO/Ag/ITO, but the structure of the first electrode is not limited thereto.

In some embodiments, an organic layer is positioned on the first electrode.

The organic layer may include at least one of a hole injection layer, a hole transport layer, a buffer layer, an emission layer, an electron transport layer, and an electron injection layer.

A hole injection layer (HIL) may be formed on the first electrode by using various methods, such as vacuum deposition, spin coating, casting, LB deposition, or the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the compound that is used to form the HIL, and the desired structure and thermal properties of the HIL to be formed. For example, the coating rate may be in the range of about 2,000 rpm to about 5,000 rpm, and a temperature at which heat treatment is performed to remove a solvent after coating may be in the range of about 80° C. to about 200° C. However, the coating conditions are not limited thereto.

For use as a hole injection material, any hole injection material suitable for use in organic light-emitting devices may be used. Non-limiting examples of the hole injection material include N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino)triphenylamine (m-MTDATA), N,N'-di(1-naphthyl)-N,N'-diphenylbenzidine (NPB), TDATA, 2-TNATA, a polyaniline/dodecylbenzenesulfonic acid (pani/DBSA), poly(3,4-ethylenedioxythiophene)/poly(4-styrenesulfonate) (PEDOT/PSS), polyaniline/camphor sulfonicacid (pani/CSA), or (polyaniline)/poly(4-styrenesulfonate) (PANI/PSS), but embodiments of the invention are not limited thereto.

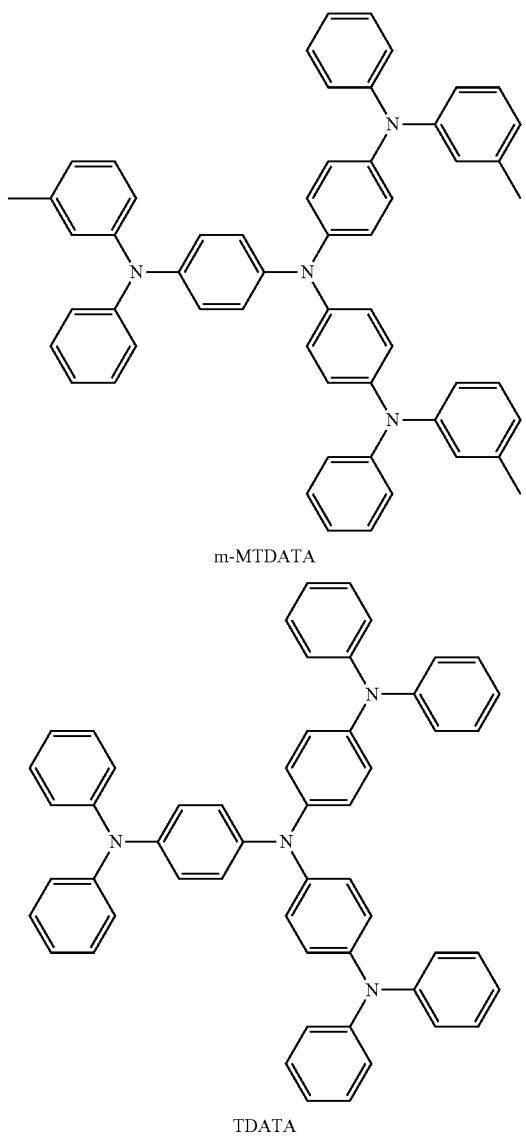

m-MTDATA

TDATA

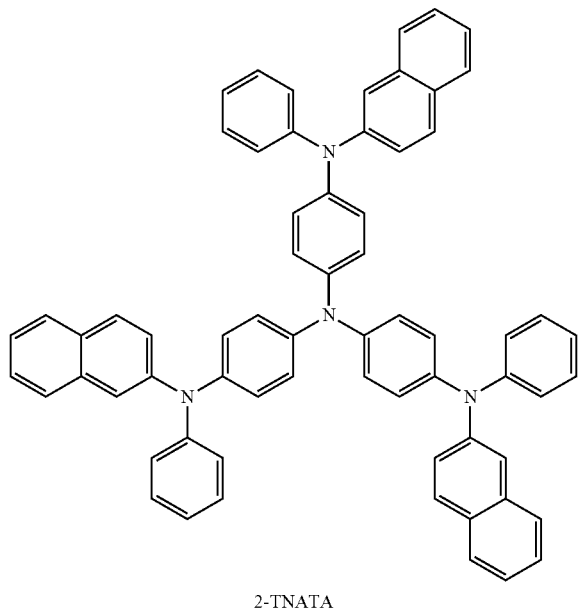

2-TNATA

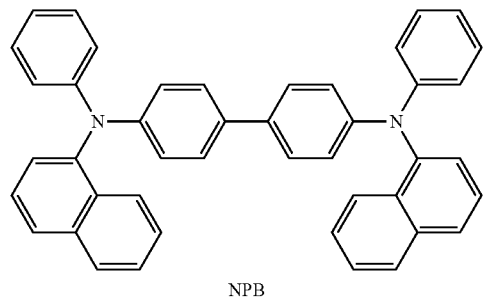

NPB

A thickness of the HIL may be in a range of about 100 Å to about 10,000 Å, and in some embodiments, may be from about 100 Å to about 1,000 Å. When the thickness of the HIL is within the range described above, the HIL may have satisfactory hole injection characteristics without a substantial increase in driving voltage.

A hole transport layer (HTL) may be formed on the HIL by using vacuum deposition, spin coating, casting, Langmuir-Blodgett (LB) deposition, or the like. When the HTL is formed using vacuum deposition or spin coating, the deposition and coating conditions may be similar to those for the formation of the HIL, though the conditions for deposition and coating may vary according to the material that is used to form the HTL.

Non-limiting examples of the hole transport material include a carbazole derivative, such as N-phenylcarbazole or polyvinylcarbazol, N,N'-bis(3-methylphenyi)-N,N'-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine (NPB), but embodiments of the invention are not limited thereto.

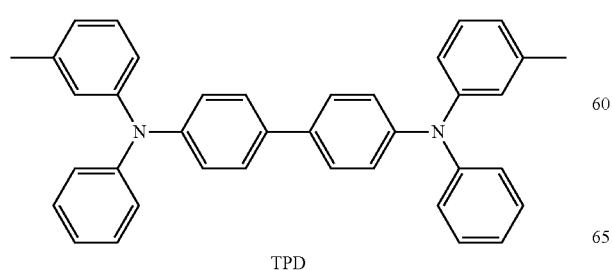

TPD

A thickness of the HTL may be in a range of about 50 Å to about 2,000 Å, and in some embodiments, may be from about 100 Å to about 1,500 Å. When the thickness of the HTL is within these ranges, the HTL may have satisfactory electron transporting ability without a substantial increase in driving voltage.

A H-functional layer (a functional layer having a hole injection ability and a hole transport ability) may include one or more materials selected from the materials for the HIL and the materials for the HTL. A thickness of the H-functional layer may be in a range of about 500 Å to about 10,000 Å, and in some embodiments, may be from about 100 Å to about 1,000 Å. When the thickness of the H-functional layer is within these ranges, the H-functional layer may have satisfactory hole injection and hole transport characteristics without a substantial increase in driving voltage.

In addition, at least one layer of the HIL, the HTL, and the H-functional layer may include at least one of a compound represented by Formula 300 below and a compound represented by Formula 350 below:

Formula 300

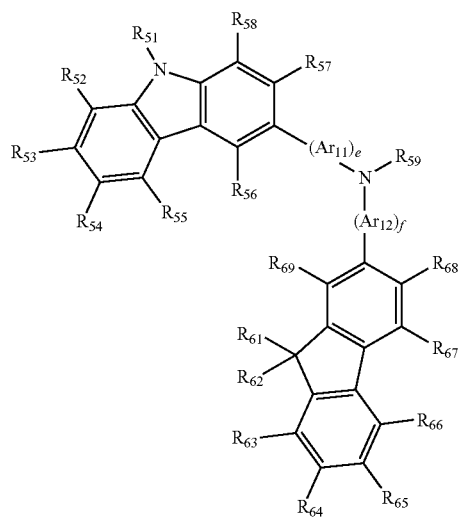

-continued

Formula 350

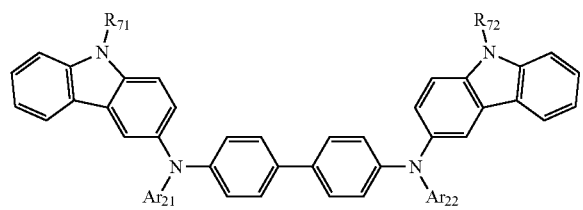

In Formula 300, $Ar_{11}$ and $Ar_{12}$ may be each independently a substituted or unsubstituted $C_6$-$C_{60}$ arylene group. For example, $Ar_{11}$ and $Ar_{12}$ may be each independently selected from a substituted or unsubstituted phenylene group, a substituted or unsubstituted naphthylene group, a substituted or unsubstituted fluorenylene group, and a substituted or unsubstituted anthrylene group, but are not limited thereto. At least one substituent of the substituted phenylene group, the substituted naphthylene group, the substituted fluorenylene group, and the substituted anthrylene group may be a deuterium atom, a halogen atom, a hydroxyl group, a cyano group, a $C_1$-$C_{20}$ alkyl group, a $C_1$-$C_{20}$ alkoxy group, a phenyl group, a naphthyl group, an anthryl group, a carbazolyl group, or a phenyl-substituted carbazolyl group, but embodiments of the invention are not limited thereto.

$Ar_{21}$ to $Ar_{22}$ in Formula 350 are each independently a substituted or unsubstituted $C_6$-$C_{60}$ aryl group or a substituted or unsubstituted $C_1$-$C_{50}$ heteroaryl group. For example, $Ar_{21}$ and $Ar_{22}$ may be each independently selected from a substituted or unsubstituted phenyl group, a substituted or unsubstituted naphthyl group, a substituted or unsubstituted phenanthrenyl group, a substituted or unsubstituted anthryl group, a substituted or unsubstituted pyrenyl group, a substituted or unsubstituted chrysenyl group, substituted or unsubstituted fluorenyl group, a substituted or unsubstituted carbazolyl group, substituted or unsubstituted dibenzofuranyl group, and a substituted or unsubstituted dibenzothiophenyl group. In some embodiments of the present invention, at least one substituent of the substituted phenyl group, the substituted naphthyl group, the substituted phenanthrenyl group, the substituted anthryl group, the substituted pyrenyl group, the substituted chrysenyl group, the substituted fluorenyl group, the substituted carbazolyl group, the substituted dibenzofuranyl group, and the substituted dibenzothiophenyl group may be selected from (i) a deuterium atom; a halogen atom; a hydroxyl group; a cyano group; a nitro group; an amino group; an amidino group; a hydrazine; a hydrazone; a carboxyl group or salt thereof; a sulfonic group or salt thereof; a phosphoric acid group or salt thereof; a $C_1$-$C_{10}$ alkyl group; and a $C_1$-$C_{10}$ alkoxy group;

(ii) a phenyl group, a naphthyl group, a fluorenyl group, a phenanthrenyl group, an anthryl group, a triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, and an indolyl group; and (iii) a phenyl group, a naphthyl group, a fluorenyl group, a phenanthrenyl group, an anthryl group, a triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, and an indolyl group, each substituted with at least one of a deuterium atom, a halogen atom, a hydroxyl group, a cyano group, a nitro group, an amino group, an amidino group, a hydrazine, a hydrazone, a carboxyl group or salt thereof, a sulfonic acid group or salt thereof, a phosphoric acid group or salt thereof, $C_1$-$C_{10}$ alkyl group, and a $C_1$-$C_{10}$ alkoxy group. In Formula 300, e and f may be each independently an integer of 0 to 5, or 0, 1 or 2. For example, e may be 1 and f may be 0, but e and f are not limited thereto.

$R_{51}$ to $R_{58}$, $R_{61}$ to $R_{69}$, and $R_{71}$ and $R_{72}$ in Formulae 300 and 350 may be each independently selected from a hydrogen atom, a deuterium atom, a halogen atom, a hydroxyl group, a cyano group, —$NO_2$, an amino group, an amidino group, hydrazine, hydrazone, a carboxyl group or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, and a substituted or unsubstituted $C_6$-$C_{60}$ arylthio group. In some embodiments, $R_{51}$ to $R_{58}$, $R_{61}$ to $R_{69}$, $R_{71}$ and $R_{72}$ may be each independently selected from (i) a hydrogen atom; a deuterium atom; a halogen atom; a hydroxyl group; a cyano group; —$NO_2$; an amino group; an amidino group; a hydrazine; a hydrazone; a carboxyl group or a salt thereof; a sulfonic acid or a salt thereof; a phosphoric acid or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like);

(ii) a $C_1$-$C_{10}$ alkyl group and a $C_1$-$C_{10}$ alkoxy group, each substituted with at least one of a deuterium atom, a halogen atom, a hydroxyl group, a cyano group, —$NO_2$, an amino group, an amidino group, a hydrazine, a hydrazone, a carboxyl group or a salt thereof, a sulfonic acid or a salt thereof and a phosphoric acid or a salt thereof;

(iii) a phenyl group; a naphthyl group; an anthryl group; a fluorenyl group; a pyrenyl group; and (iv) a phenyl group, a naphthyl group, an anthryl group, a fluorenyl group, and a pyrenyl group, each substituted with at least one of a deuterium atom, a halogen atom, a hydroxyl group, a cyano group, —$NO_2$, an amino group, an amidino group, hydrazine, hydrazone, a carboxyl group or a salt thereof, a sulfonic acid or a salt thereof, a phosphoric acid or a salt thereof, a $C_1$-$C_{10}$ alkyl group, and a $C_1$-$C_{10}$ alkoxy group, but $R_{51}$ to $R_{58}$, $R_{61}$ to $R_{69}$, $R_{71}$ and $R_{72}$ are not limited thereto.

$R_{59}$ in Formula 300 may be selected from a phenyl group; a naphthyl group; an anthryl group; a biphenyl group; and a pyridyl group; and a phenyl group, a naphthyl group, an anthryl group, a biphenyl group, and a pyridyl group, each substituted with at least one of a deuterium atom, a halogen atom, a hydroxyl group, a cyano group, —$NO_2$, an amino group, an amidino group, hydrazine, hydrazone, a carboxyl group or a salt thereof, a sulfonic acid or a salt thereof, a phosphoric acid or a salt thereof, a substituted or unsubstituted $C_1$-$C_{20}$ alkyl group, and a substituted or unsubstituted $C_1$-$C_{20}$ alkoxy group.

According to an embodiment of the present invention, the compound represented by Formula 300 may be represented by Formula 300A, but the chemical structure of the compound is not limited thereto:

Formula 300A
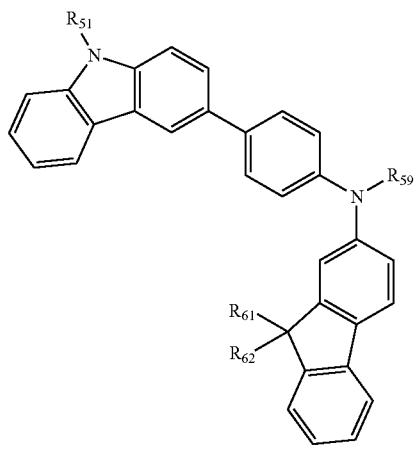
Detailed descriptions of $R_{51}$, $R_{61}$, $R_{62}$, and $R_{59}$ in Formula 300A are the same as described above in connection with Formula 300.
In some embodiments, at least one layer of the HIL, the HTL, and the H-functional layer may include at least one of Compounds 301 to 320 below, but is not limited thereto.
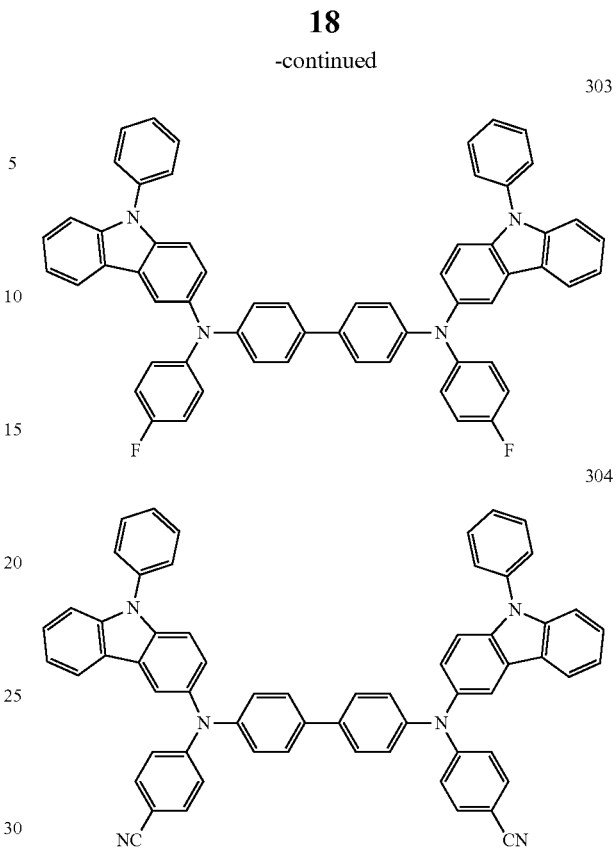
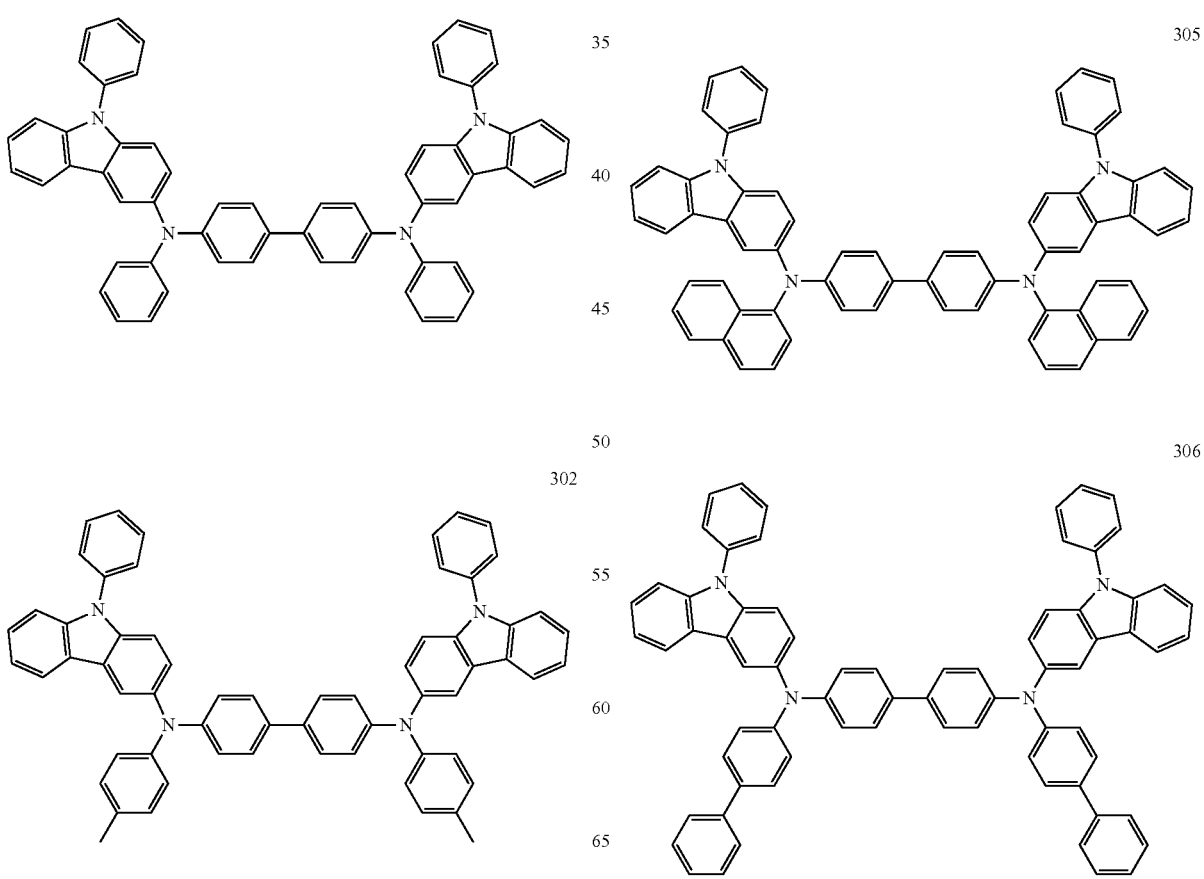

307
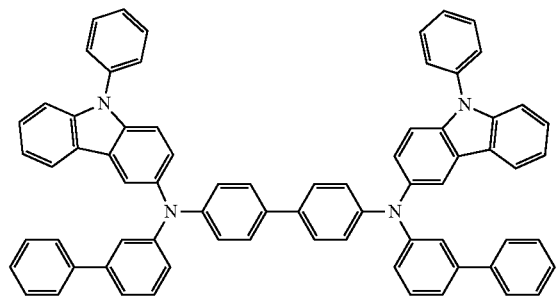
308
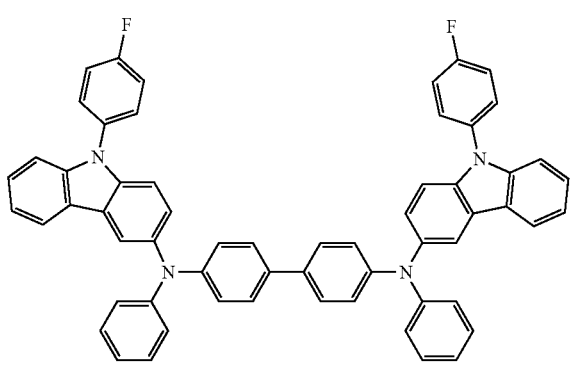
309
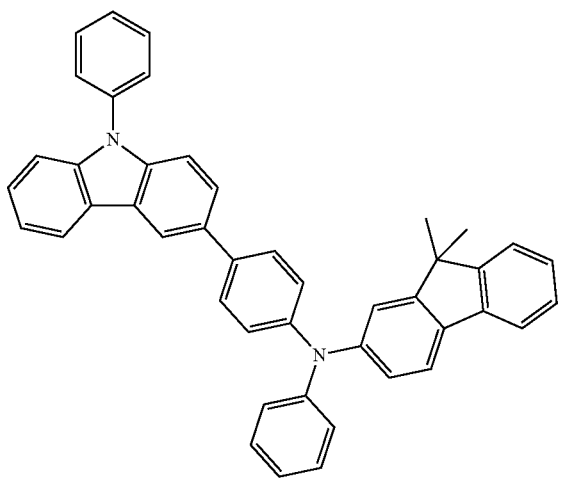
310
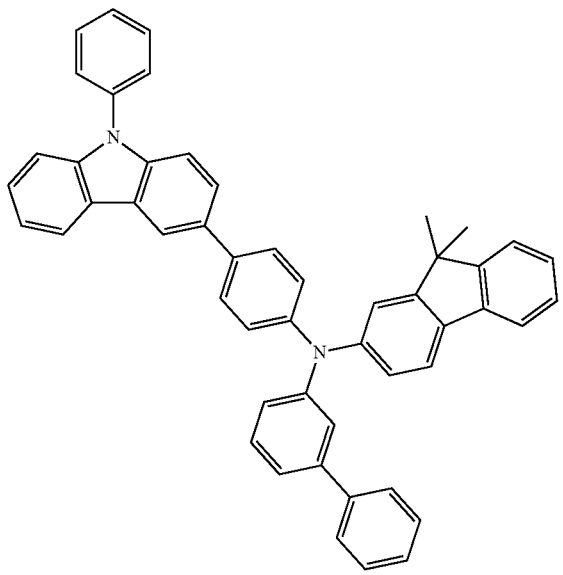
311
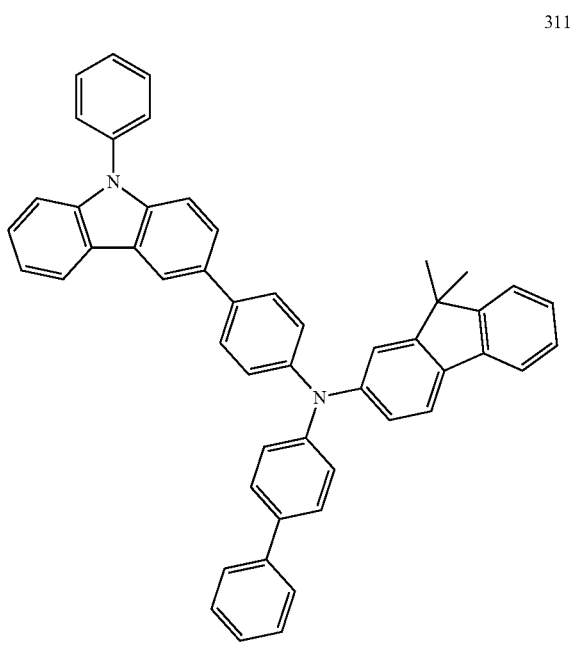

312
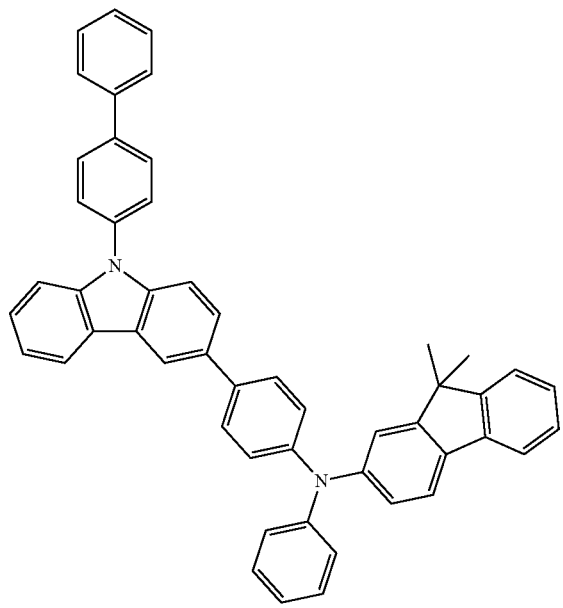
313
314
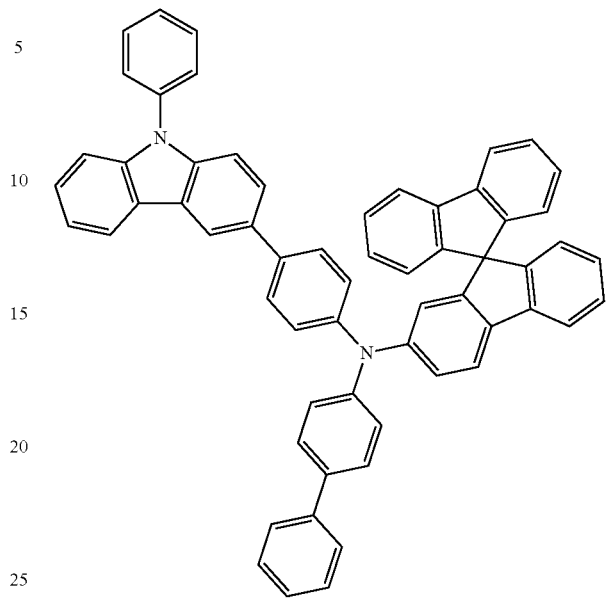
315

-continued

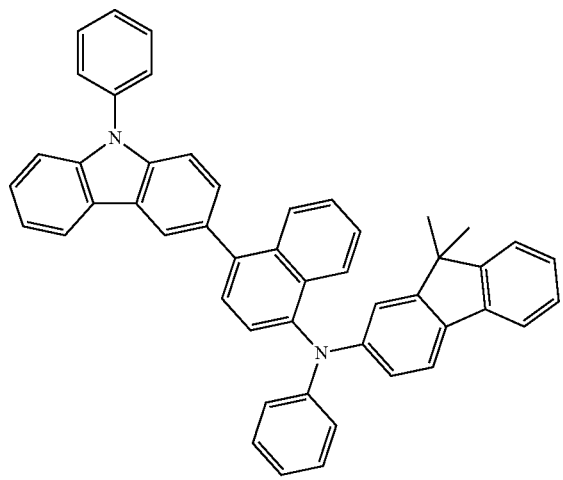
316

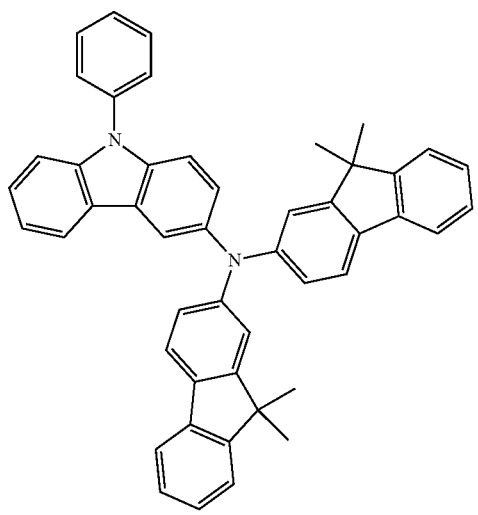
317

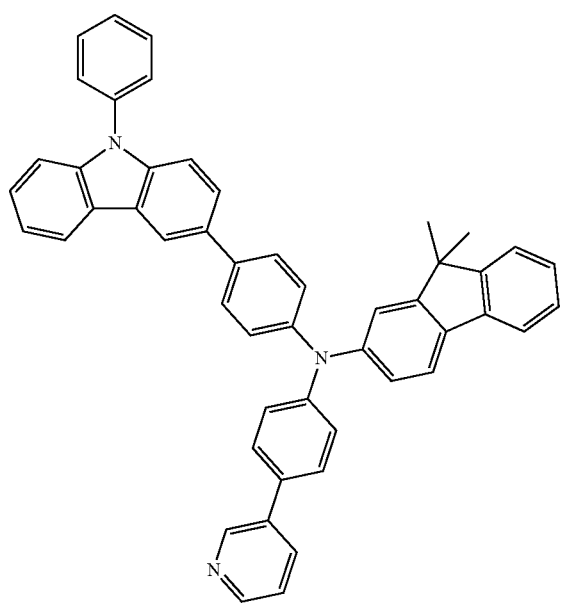
318

-continued

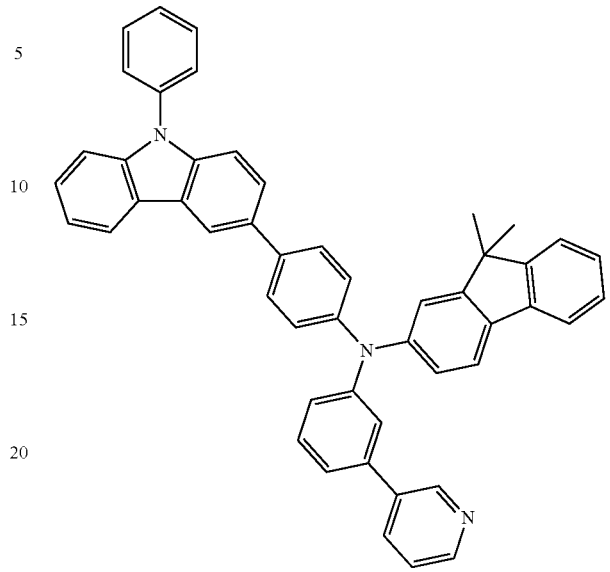
319

320

At least one of the HIL, the HTL, and the H-functional layer may further include a charge-generating material to increase conductivity of a layer, in addition to the hole injecting materials, the hole transport materials, and/or the materials having both hole injection and hole transport capabilities as described above.

The charge-generation material may be, for example, a p-dopant. The p-dopant may be one of a quinone derivative, a metal oxide, and a cyano group-containing compound, but is not limited thereto. Non-limiting examples of the p-dopant are a quinone derivative, such as tetracyanoquinonedimethein (TCNQ), 2,3,5,6-tetrafluoro-tetracyano-1,4-benzoquinonedimethein (F4-TCNQ), or the like; a metal oxide, such as a tungsten oxide and a molybdenum oxide; and a cyano group-containing compound, such as Compound 200 below, but are not limited thereto.

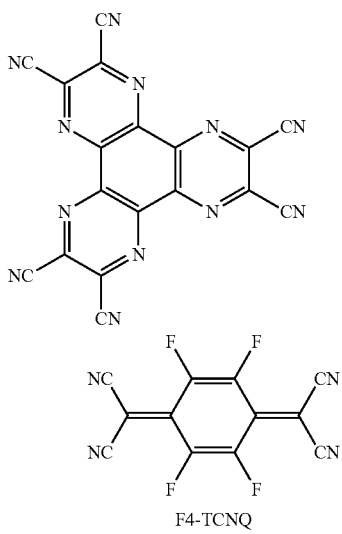

Compound 200

F4-TCNQ

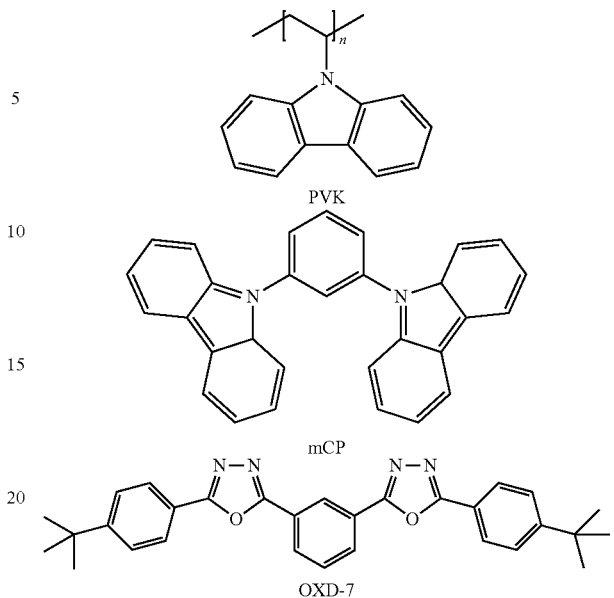

PVK mCP

OXD-7

When the HIL, the HTL or the H-functional layer further includes a charge-generating material, the charge-generating material may be homogeneously dispersed or non-homogeneously distributed in the HIL, the HTL, and the H-functional layer.

A buffer layer may be positioned between at least one of the HIL, the HTL, and the H-functional layer, and an emission layer. The buffer layer may compensate for an optical resonance distance of light according to a wavelength of the light emitted from the emission layer, and thus may increase efficiency of the organic light-emitting device. The buffer layer may include any hole injecting material or hole transporting material suitable for use in organic light-emitting devices. In some embodiments, the buffer layer may include the same material as one of the materials included in the HIL, the HTL, and the H-functional layer.

An emission layer (EML) may be formed on the HTL, the H-functional layer, or the buffer layer by vacuum deposition, spin coating, casting, or a LB method. When the EML is formed by vacuum deposition or spin coating, the deposition and coating conditions may be similar to those for the formation of the HIL, though the conditions for deposition and coating may vary according to the material that is used to form the EML.

The EML may include at least one iridium complex.

The iridium complex included in the EML may act as a dopant (for example, a green phosphorescent dopant or a blue phosphorescent dopant). In some embodiments, the EML may further include a host, in addition to the iridium complex.

The host may be at least one selected from any host suitable for use in organic light-emitting devices. Non-limiting examples of the host include $Alq_3$, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl) anthracene (TBADN), mCP, or OXD-7, but embodiments of the invention are not limited thereto.

In an embodiment of the present invention, the host may be a carbazole-based compound represented by Formula 10:

Formula 10

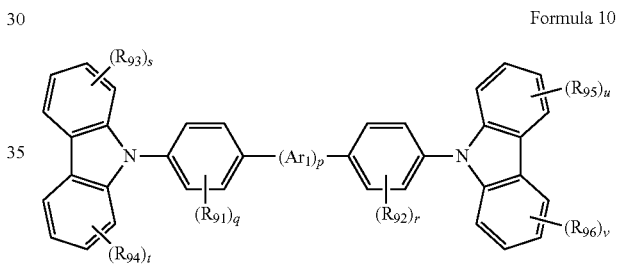

In Formula 10, $Ar_1$ may be selected from a substituted or unsubstituted $C_1$-$C_{60}$ alkylene group, a substituted or unsubstituted $C_2$-$C_{60}$ alkenylene group, —C(=O)—, —N($R_{100}$)— (wherein $R_{100}$ is a substituted or unsubstituted $C_6$-$C_{60}$ aryl group, or a substituted or unsubstituted $C_1$-$C_{60}$ heteroaryl group), a substituted or unsubstituted $C_6$-$C_{60}$ arylene group, or a substituted or unsubstituted $C_2$-$C_{60}$ heteroarylene group; p is an integer of 0 to 10; $R_{91}$ to $R_{96}$ may be each independently selected from a hydrogen atom, a deuterium atom, a halogen atom, a hydroxyl group, a cyano group, a nitro group, an amino group, an amidino group, a hydrazine, a hydrazone, a carboxyl group or salt thereof, a sulfonic group or salt thereof, a phosphoric acid group or salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_1$-$C_{60}$ heteroaryl group, and adjacent two substituents of $R_{91}$ to $R_{96}$ may bind to each other to form a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic ring, or a substituted or unsubstituted $C_2$-$C_{20}$ heteroaromatic ring; and q, r, s, t, u, and v may be each independently an integer of 1 to 4.

In some embodiments, $Ar_1$ may be a $C_1$-$C_5$ alkylene group, a $C_2$-$C_5$ alkenylene group, —C(=O)—, or —N($R_{100}$), wherein $R_{100}$ may be one selected from a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group, each substituted with at least one of a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group.

In some embodiments, $R_{91}$ to $R_{96}$ may be each independently selected from a hydrogen atom, a deuterium atom, a halogen atom, a hydroxyl group, a cyano group, a nitro group, an amino group, an amidino group, a hydrazine, a hydrazone, a carboxyl group or salt thereof, a sulfonic acid group or salt thereof, a phosphoric acid group or salt thereof, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one of a deuterium atom, a halogen atom, a hydroxyl group, a cyano group, a nitro group, and an amino group.

For example, the carbazole-based compound of Formula 10 may be one of the Compounds H1-H30, but is not limited thereto:

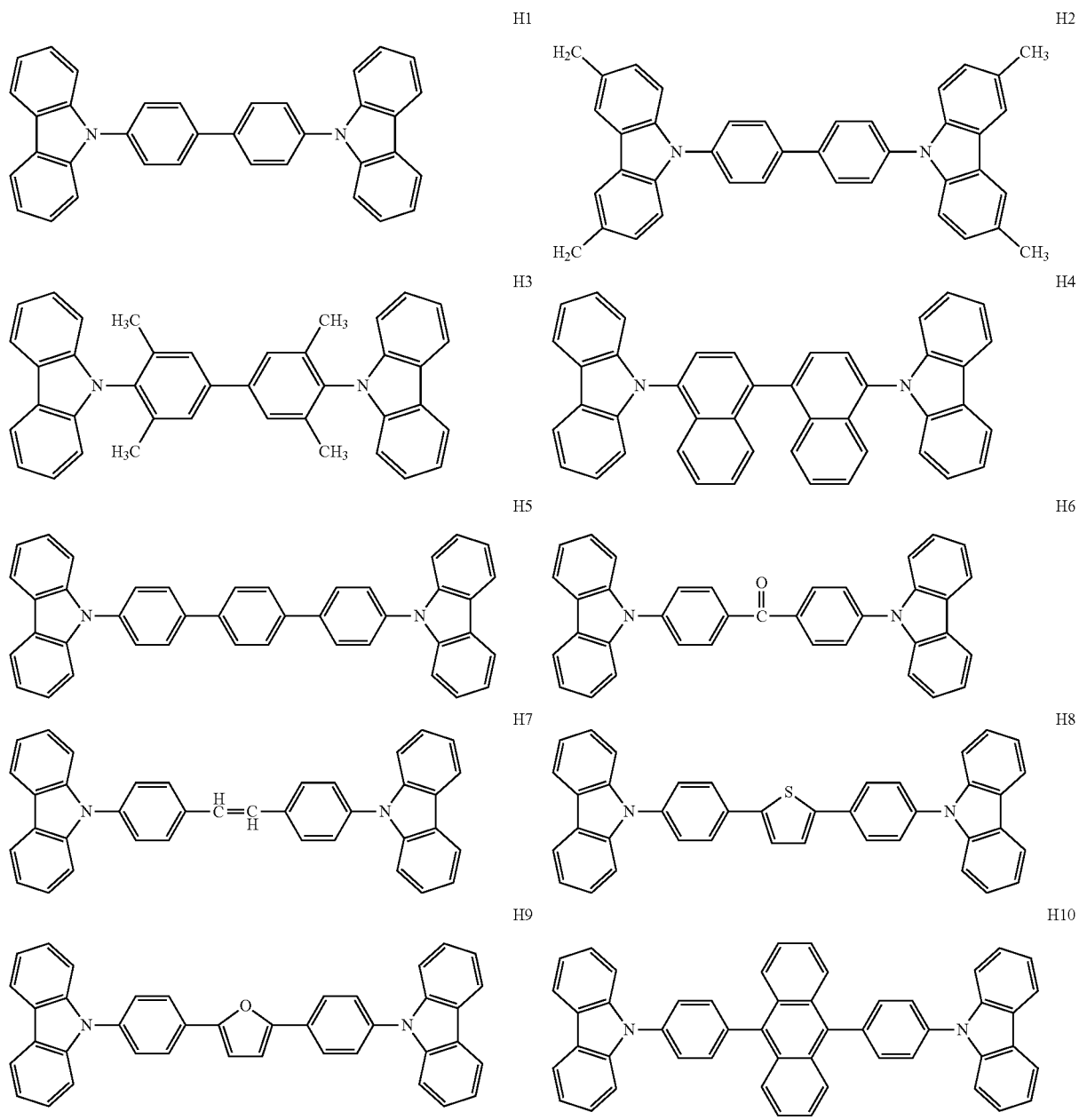

-continued
H11
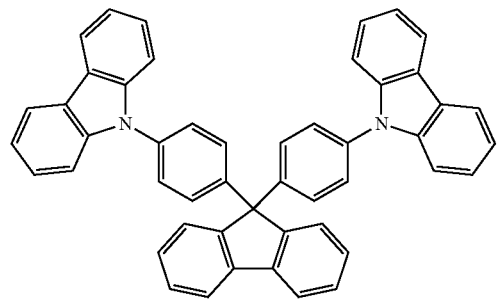
H12
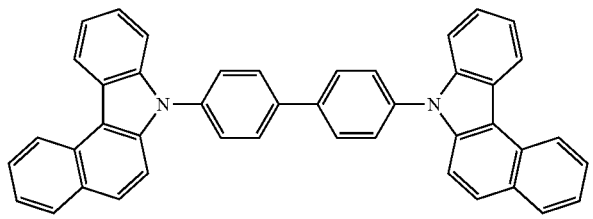
H13
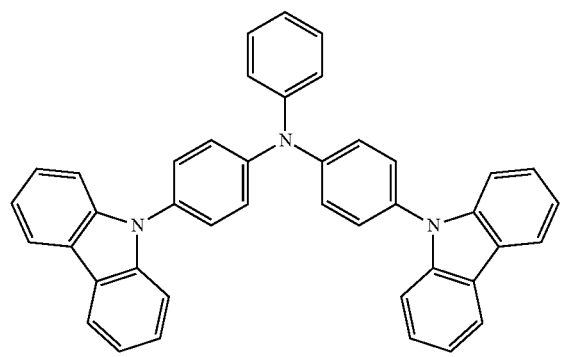
H14
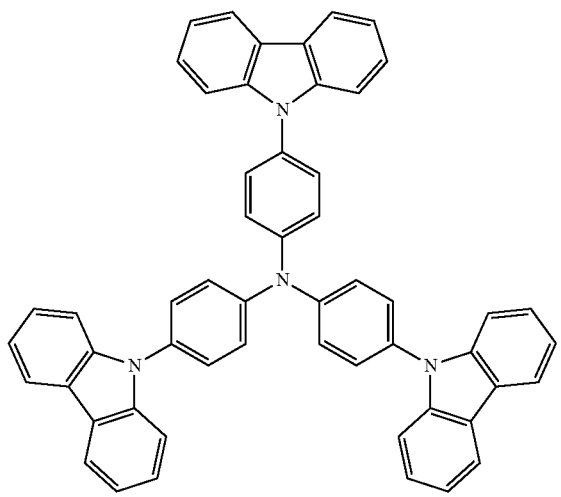
H15
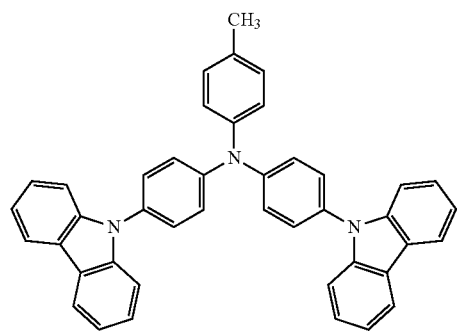
H16
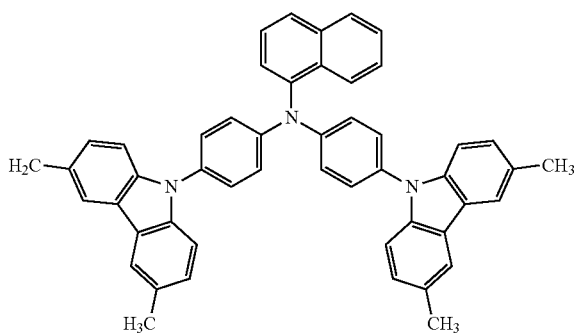
H17
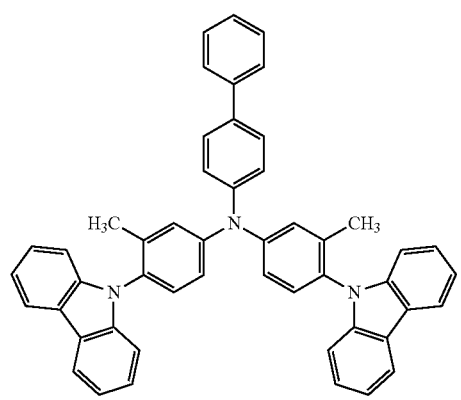
H18
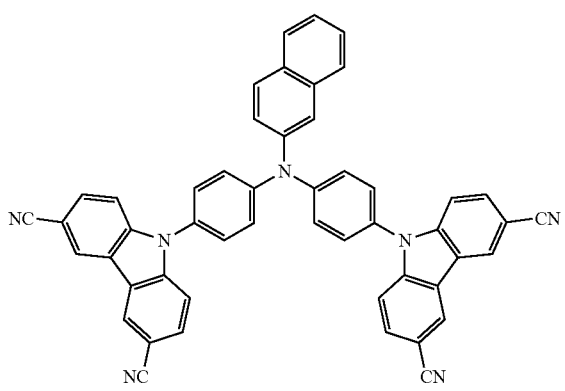

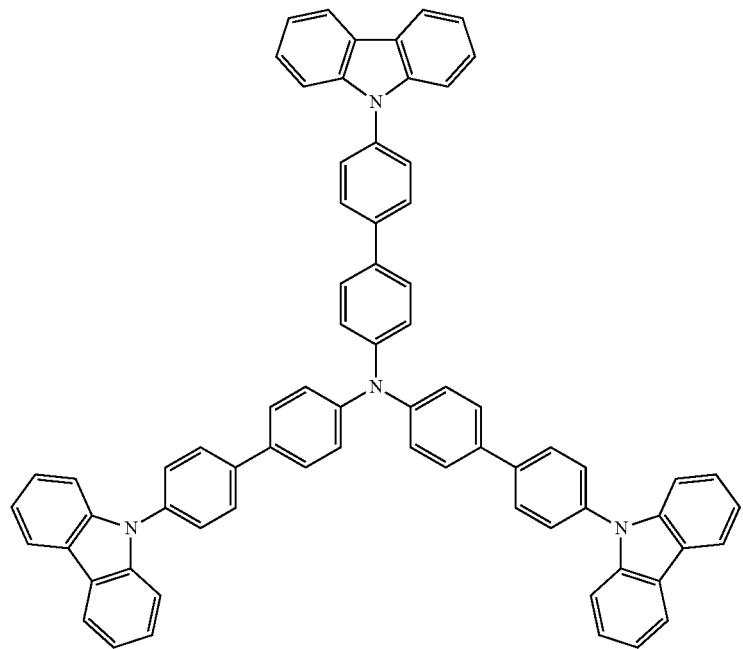
H19
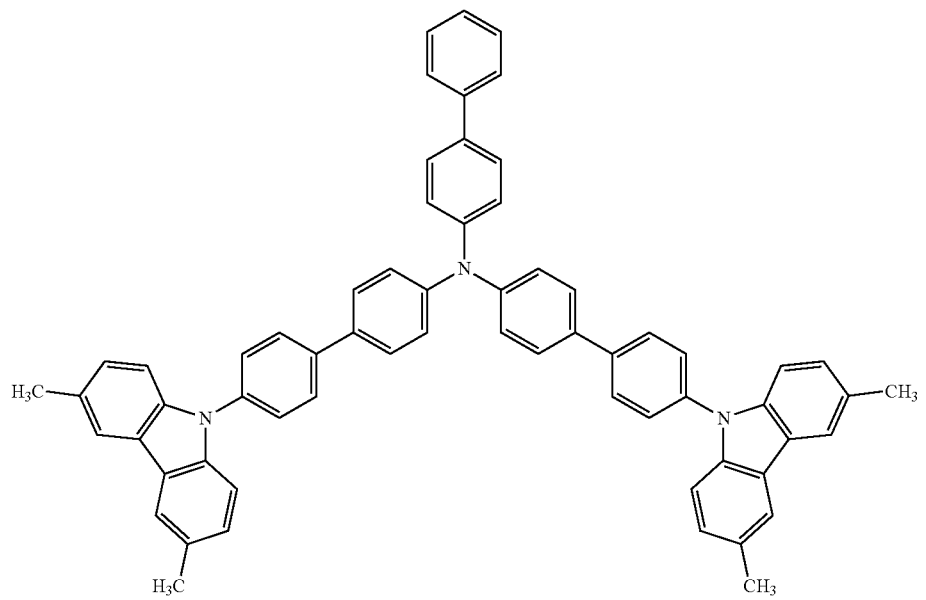
H20

H21
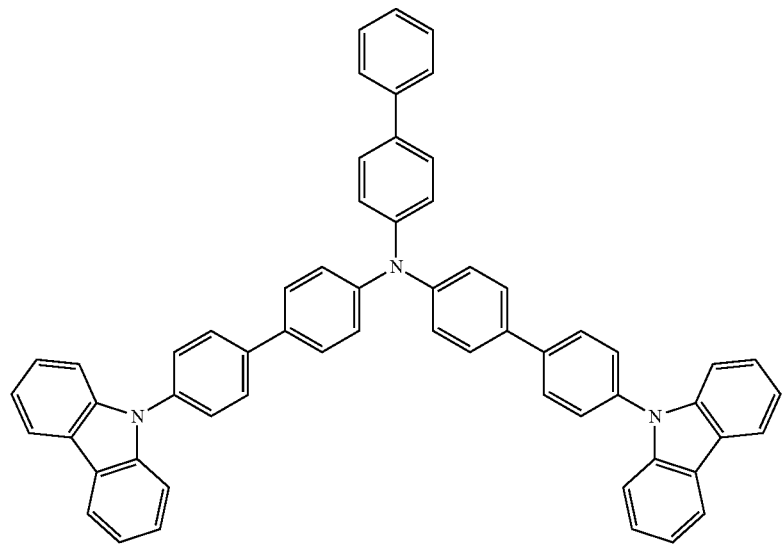
H22
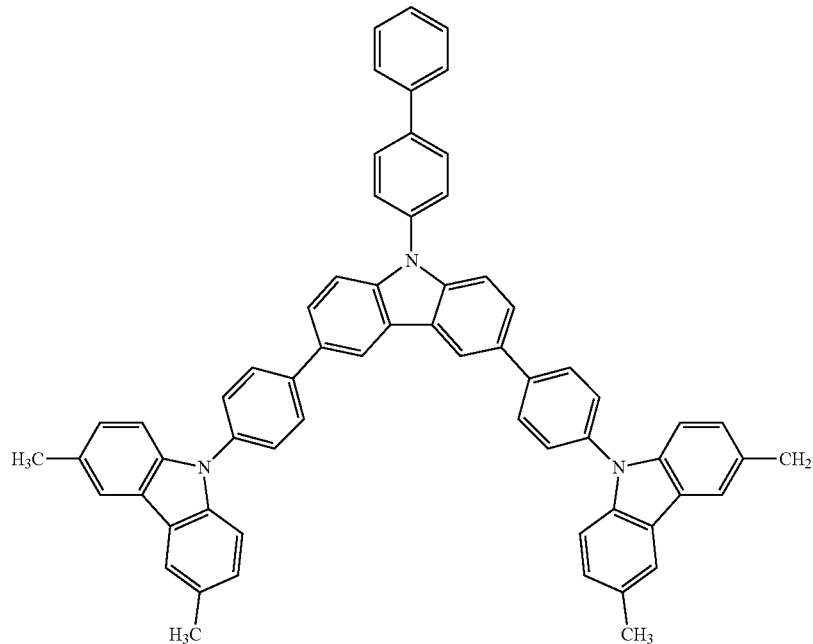
H23
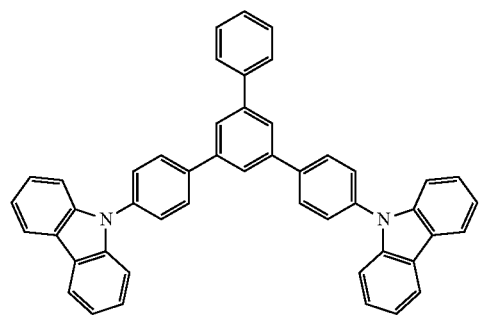
H24
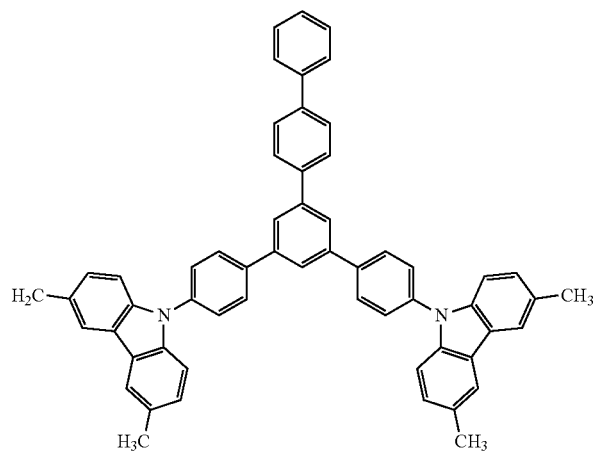

-continued

H25
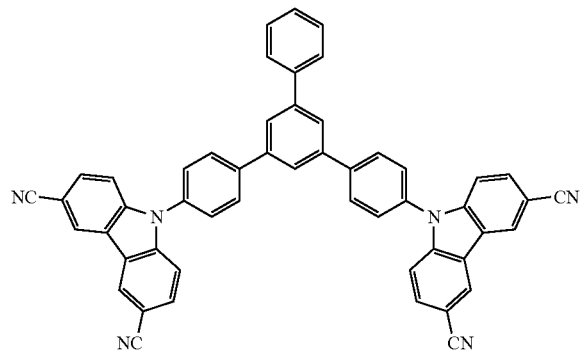

H26
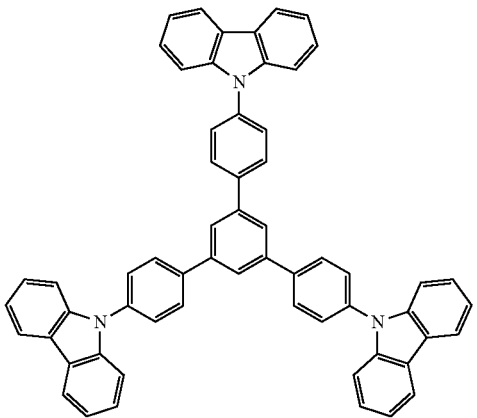

H27
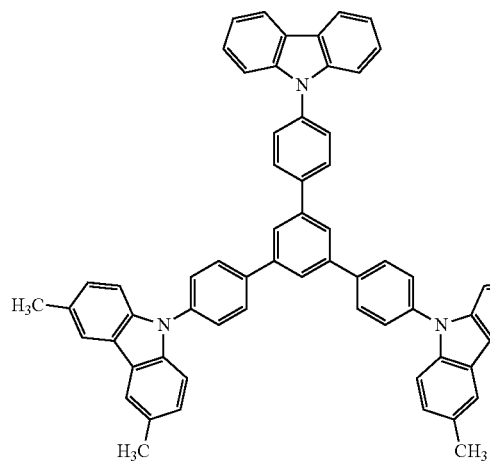

H28
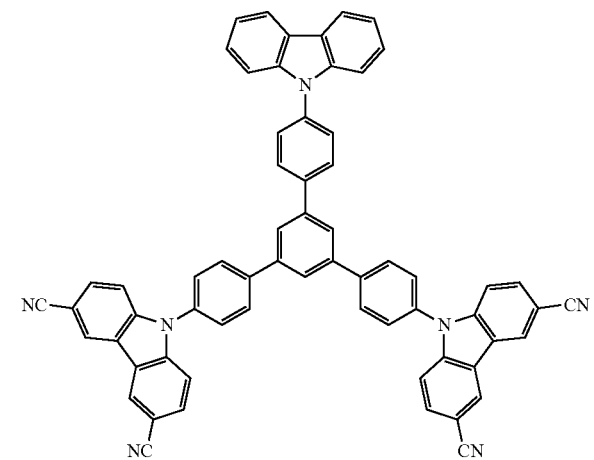

H29
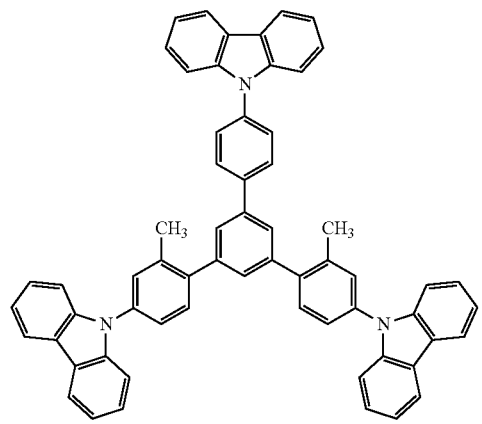

H30
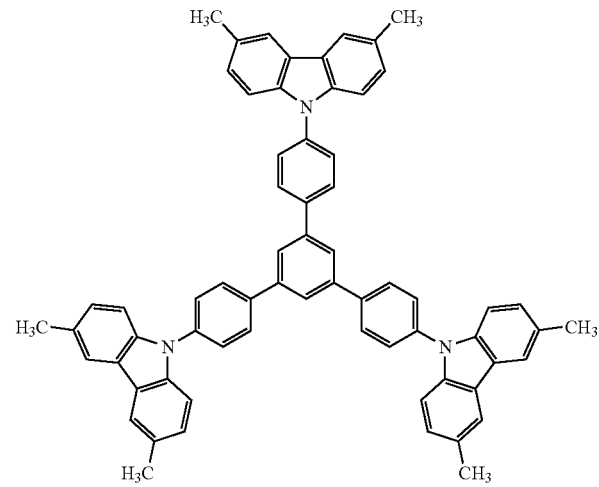

When the EML includes a host and a dopant including the iridium complex represented by Formula 1, an amount of the dopant may be in a range from about 0.01 to about 15 wt % based on 100 wt % of the EML. In some embodiments, an amount of the dopant may be in a range from about 1 to about 15 wt % based on 100 wt % of the EML, but is not limited thereto.

A thickness of the EVIL may be in a range from about 200 Å to about 700 Å. When the thickness of the EML is within this range, the EML may have improved luminescent properties without a substantial increase in driving voltage.

An electron transport layer (ETL) may be formed on the EML by using various methods, for example, by vacuum deposition, spin coating, casting, or the like. When the ETL is formed using vacuum deposition or spin coating, the deposition and coating conditions may be similar to those for the formation of the HIL, though the conditions for deposition and coating may vary according to the material that is used to form the ETL. A material for forming the ETL may stably transport electrons injected from an electron injection electrode (cathode), and may be any electron transportation material suitable for use in organic light-emitting devices. Non-limiting examples of the material for the electron transport layer include a quinoline derivative, such as tris(8-quinolinolate)aluminium (Alq3), TAZ, Balq, beryllium bis(benzoquinolin-10-olate) (Bebq₂), ADN, Compound 101, Compound 102, bathocuproine (BCP) and Bphen, but embodiments of the invention are not limited thereto.

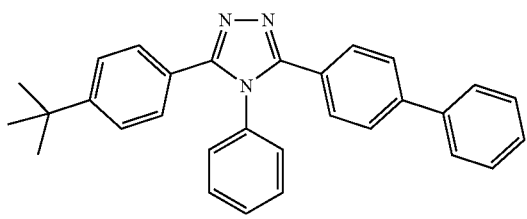

TAZ

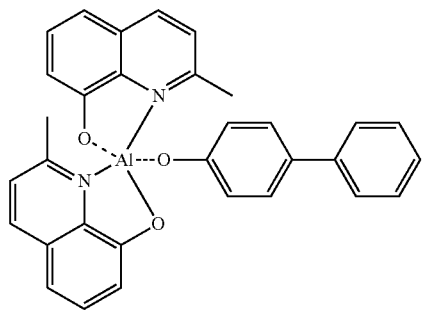

BAlq

Compound 101

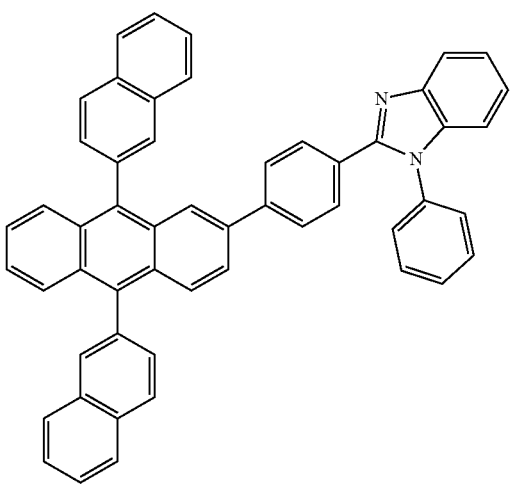

Compound 102

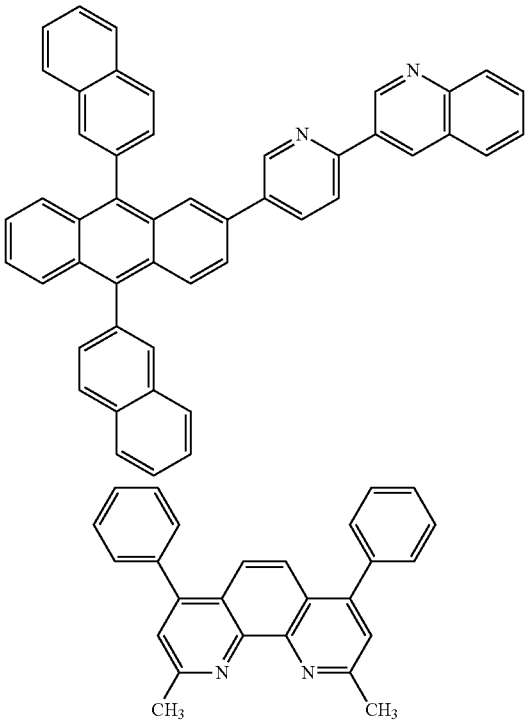

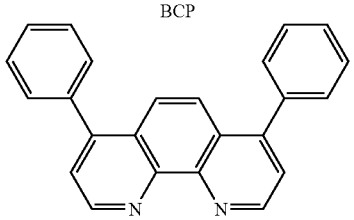

BCP

Bphen

A thickness of the ETL may be in a range from about 100 Å to about 1,000 Å, and in some embodiments, from about 150 Å to about 500 Å. When the thickness of the ETL is within these ranges, the ETL may have satisfactory electron transporting ability without a substantial increase in driving voltage.

The ETL may include, in addition to the electron transportation organic compound, a metal-containing material.

The metal-containing material may include a lithium (Li) complex. Non-limiting examples of the Li complex are lithium quinolate (Liq) and Compound 203 below:

Compound 203

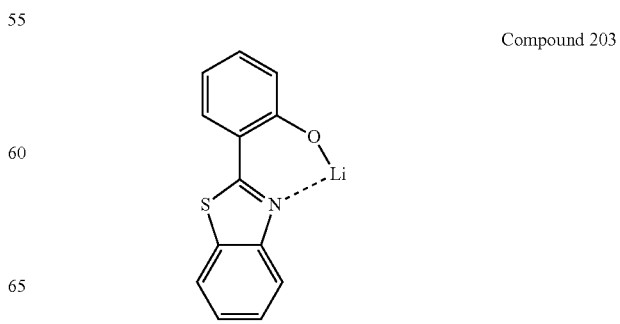

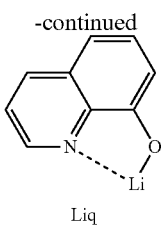

Liq

An electron injection layer (EIL), which in some embodiments facilitates injection of electrons from the cathode, may be formed on the ETL. Any suitable electron-injecting material may be used to form the EIL.

Non-limiting examples of materials for forming the EIL are LiF, NaCl, CsF, $Li_2O$, and BaO. The deposition conditions of the EIL may be similar to those used to form the HIL, although the deposition conditions may vary according to the material that is used to form the EIL.

A thickness of the EIL may be from about 1 Å to about 100 Å, and in some embodiments, may be from about 3 Å to about 90 Å. When the thickness of the EIL is within these ranges, the EIL may have satisfactory electron injection ability without a substantial increase in driving voltage.

A second electrode is may be positioned on the organic layer. The second electrode may be a cathode, which in some embodiments is an electron injection electrode, and a material for forming the second electrode may be metal, alloy, an electrically conductive compound, or a mixture thereof, each of which has a low work function. Non-limiting examples of the material for forming the second electrode are lithium (Li), magnesium (Mg), aluminum (Al), aluminum-lithium (Al—Li), calcium (Ca), magnesium-indium (Mg—In), or magnesium-silver (Mg—Ag), and these materials may be formed in a thin film to form a transmissive electrode. In some embodiments, to manufacture a top-emission light-emitting device, indium tin oxide (ITO) or indium zinc oxide (IZO) may be used to form a transmissive electrode.

Hereinbefore, the organic light-emitting device has been described with reference to FIG. 3, but embodiments of the invention are not limited thereto.

In the embodiments when the EML includes a phosphorescent dopant, a hole blocking layer (HBL) may be formed between the HTL and the EML or between the E-functional layer and the EML by vacuum deposition, spin coating, casting, LB deposition, etc. so as to prevent diffusion of triplet excitons or holes into the ETL. When the HBL is formed by vacuum deposition or spin coating, the deposition and coating conditions may be similar to those for the formation of the HIL, though the conditions for deposition and coating may vary according to the material that is used to form the HBL. Any hole-blocking material suitable for use in organic light-emitting devices may be used. Examples thereof are oxadiazole derivatives, triazole derivatives, and phenanthroline derivatives. For example, bathocuproine (BCP) illustrated below may be used as a hole-blocking material.

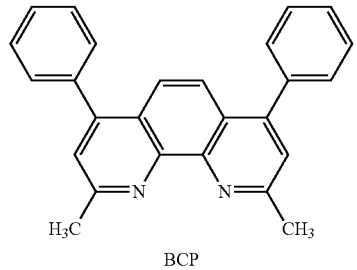

BCP

A thickness of the HBL may be in a range from about 20 Å to about 1000 Å, and in some embodiments, from about 30 Å to about 300 Å. When the thickness of the HBL is within these ranges, the HBL may have improved hole blocking properties without a substantial increase in driving voltage.

Hereinafter, one or more embodiments of the present invention will be described in detail with reference to the following examples. These examples are not intended to limit the purpose and scope of the one or more embodiments of the present invention.

EXAMPLE

Synthesis Example 1

Synthesis of Complex 1

Synthesis of Intermediate 1-1

Intermediate 1-1 was synthesized according to Reaction Scheme 1(1):

Reaction Scheme 1(1)

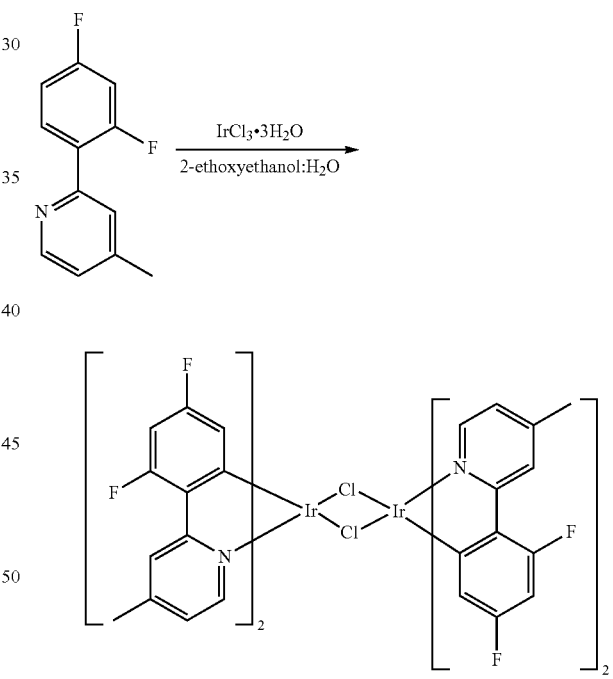

Dimer 1-1

3.6 g (17.3 mmol) of 2-(2,4-difluorophenyl)-4-methyl-pyridine was dissolved in 45 mL of 2-ethoxyethanol, and then, 2.4 g (7.6 mmol) of iridium chloride hydrate and 15 mL of distilled water were added thereto, and the mixture was stirred at a temperature of 130° C. for 20 hours. When the reaction was terminated, the reaction solution was cooled to room temperature, and a precipitate was collected and then, the precipitate was washed with methanol and dried in a vacuum condition to prepare 4.3 g (60%) of Intermediate 1-1, which is a dimer.

Synthesis of Complex 1

Complex 1 was synthesized by wet chemistry (e.g. wet process) according to Reaction Scheme 1(2):

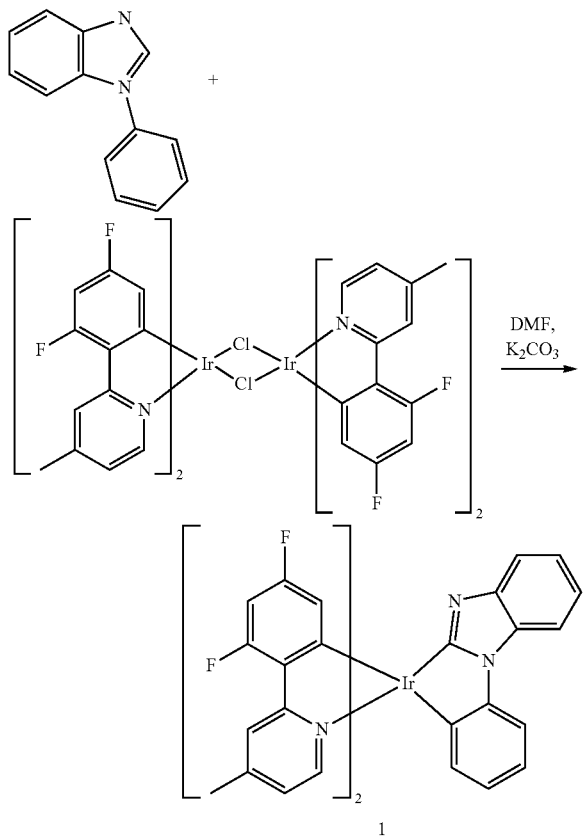

Reaction Scheme 1(2)

1.0 g (1.03 mmol) of Intermediate 1-1 obtained according to Reaction Scheme 1(1), 0.48 g (2.44 mmol) of phenyl benzoimidazole, and 0.34 g (2.46 mmol) of $K_2CO_3$ were added to 30 mL of 2-ethoxyethanol, and then, the mixture was stirred at a temperature of 130 t for 12 hours. When the reaction was terminated, the reaction solution was cooled to room temperature, and a precipitate was collected and then, the precipitate was washed with methanol. The precipitate was melted in dichloromethane and then filtered by using a silica short pad. The filtered dichloromethane solution was boiled and methanol was added thereto in small amounts to precipitate 0.60 g (53%) of a phosphorescent compound represented by Formula 1.

Evaluation Example 1

Luminescent Characteristics Evaluation of Complex 1 in Solution

The UV absorption spectrum and photoluminescence (PL) spectrum of Complex 1 synthesized according to Synthesis Example 1 were evaluated to identify luminescent characteristics of Complex 1. First, Complex 1 was diluted in toluene up to a concentration of 0.2 mM to measure the UV absorption spectrum of Complex 1 in solution by using Shimadzu UV-350 Spectrometer.

Separately, Complex 1 was diluted in toluene up to a concentration of 10 mM, and then, the PL spectrum of Complex 1 in solution was measured by using a Xenon-lamp equipped ISC PC1 spectrofluorometer. Results thereof are shown in FIGS. 1 and 2.

Figure 2:
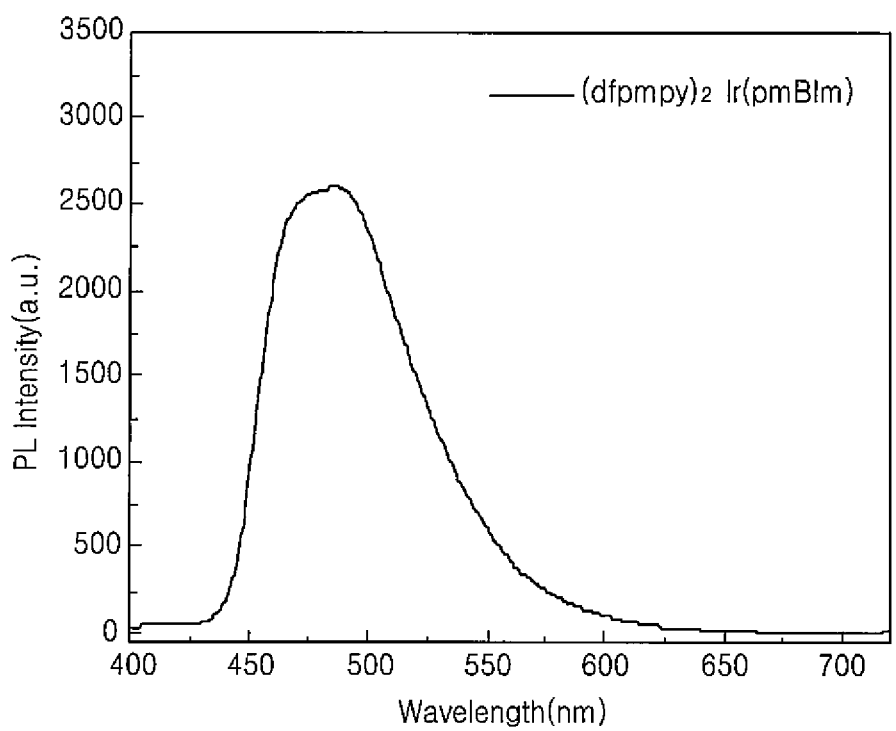
FIG. 2 is a photoluminescence (PL) spectrum of Complex 1.

Referring to FIGS. 1 and 2, it was confirmed that Complex 1 had excellent UV absorption characteristics and PL luminescent characteristics.

Example 1

An anode was manufactured as follows: a Corning 15 $\Omega/cm^2$ (1200 Å) ITO glass substrate was cut to a size of 50 mm×50 mm×0.7 mm, and then sonicated with isopropyl alcohol and pure water each for 5 minutes, and then washed by irradiation of ultraviolet ray for 30 minutes and ozone, and the result glass substrate was provided to a vacuum deposition apparatus.

2-TNATA, which is a known material, was vacuum deposited on the substrate to form a HIL having a thickness of 600 Å, and then, 4,4'-bis[N-(1-naphthyl)-N-phenylamino] biphenyl (NPB), which is a known hole transportation compound, was vacuum deposited thereon to form a HTL having a thickness of 300 Å.

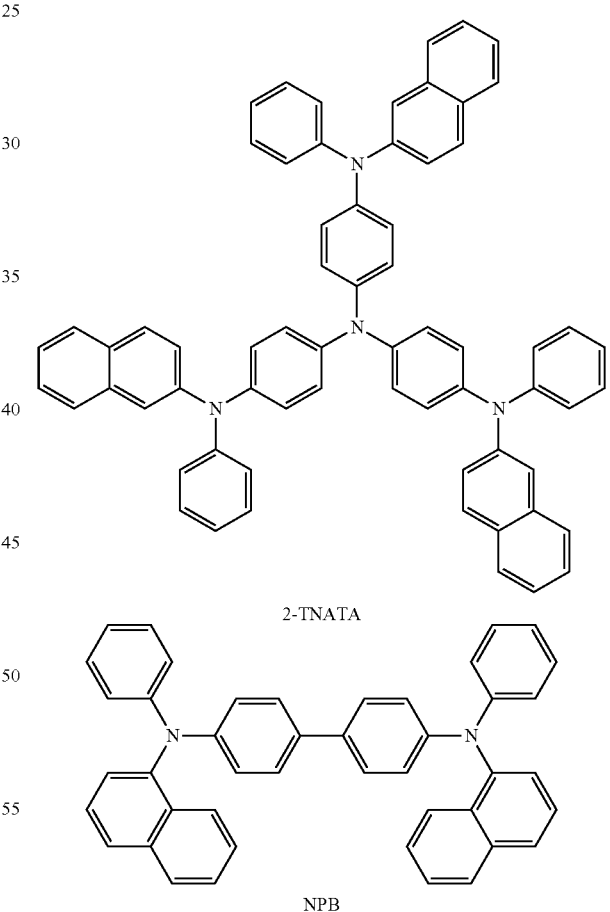

2-TNATA

NPB

CBP, which is a known phosphorescent host and iridium Complex 1 according to an embodiment of the present invention were co-deposited thereon at a weight ratio 98:2 to form an EML having a thickness of 400 Å. Subsequently, Compound 101 was deposited on the EML to form an ETL having a thickness of 300 Å. Then, LiF, which is a halogenated alkali metal, was deposited on the ETL to form an EIL having a thickness of 10 Å, and Al was vacuum deposited to form a cathode having a thickness of 3000 Å thus forming an LiF/Al electrode and completing manufacturing of an organic electroluminescent light-emitting device.

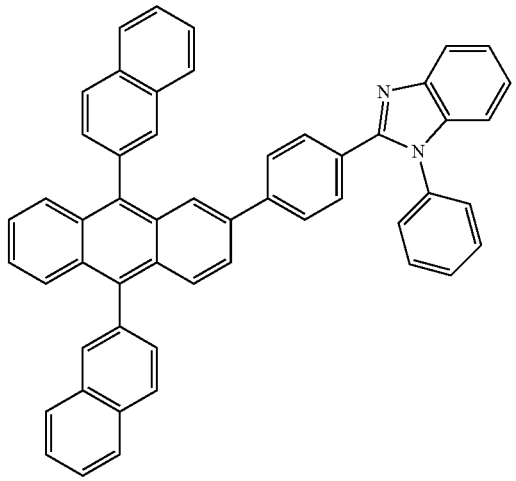

Example 2

An organic EL device was manufactured in the same manner as in Example 1, except that in forming the EML, Compound 2 was used instead of Compound 1.

Example 3

An organic EL device was manufactured in the same manner as in Example 1, except that in forming the EML, Compound 3 was used instead of Compound 1.

Comparative Example 1

An organic EL device was manufactured in the same manner as in Example 1, except that in forming the EML, Compound 102, which is a known material, was used instead of Compound 1.

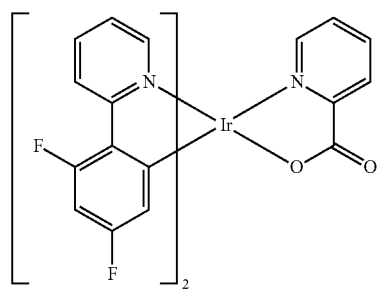

Comparative Example 2

An organic EL device was manufactured in the same manner as in Example 1, except that in forming the EML, Compound 103, which is a known material, was used instead of Compound 1.

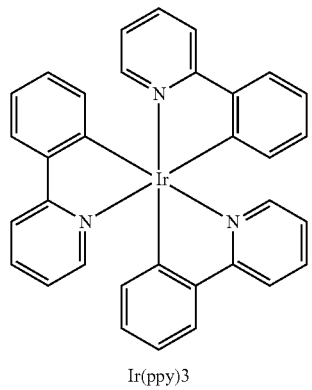

Ir(ppy)3

Evaluation Example 2

The efficiency and color purity of the organic light-emitting devices manufactured according to Examples 1 to 3 and Comparative Examples 1 and 2 were evaluated by using a PR650 Spectroscan Source Measurement Unit (a product of PhotoResearch company). Results thereof are shown in Table 1:

TABLE 1

|  | Dopant | Efficiency (cd/A) at 10 mA/m$^2$ | Color coordinate |
| --- | --- | --- | --- |
| Example 1 | Compound 1 | 25.2 | 0.21, 0.35 |
| Example 2 | Compound 2 | 24.8 | 0.22, 0.36 |
| Example 3 | Compound 3 | 23.1 | 0.22, 0.36 |
| Comparative Example 1: | Compound 102 | 22.5 | 0.17, 0.35 |
| Comparative Example 2: | Compund 103 | 22.4 | 0.28, 0.50 |

Compounds 1-3 according to an embodiment of the present invention were used as a blue light-emitting material in an organic light-emitting device. As a result, it was confirmed that all the compounds had higher efficiency than Compounds 102 and 103, which are known materials.

As described above, according to the one or more of the above embodiments of the present invention, A phosphorescent Ir complex, according to embodiments of the present invention, has improved light-emitting characteristics, may embody various colors from green to blue, and is suitable for use as a light-emitting material for a phosphorescent device. Accordingly, due to the inclusion of the heterocyclic material according to embodiments of the present invention, an organic light-emitting device having high efficiency, low voltage, high brightness and long lifespan may be manufactured.

Additionally, the phosphorescent Ir complex according to an embodiment of the present invention has a high glass transition temperature (Tg) and a high melting point. Accordingly, during electroluminescent light-emission, a resistance against Joule heating in an emission layer (organic layer), between organic layers, or between an organic layer and a metal electrode, and a resistance under high-temperature environments may increase. An organic electroluminescent light-emitting device manufactured by using the compound described herein may have high durability during storage and driving.

It should be understood that the exemplary embodiments described therein should be considered in a descriptive sense only and not for purposes of limitation. Descriptions of features or aspects within each embodiment should typically be considered as available for other similar features or aspects in other embodiments or equivalents thereof.

What is claimed is:

1. An iridium complex represented by Formula 1 below:

Formula 1

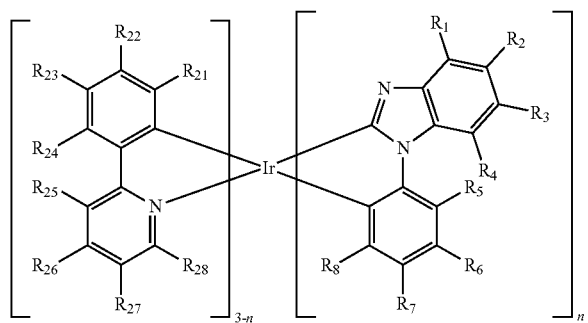

where each of $R_1$ to $R_8$ and $R_{21}$ to $R_{28}$ is independently selected from a hydrogen atom, a deuterium atom, a halogen, a hydroxyl group, a cyano group, a nitro group, an amino group, an amidino group, a hydrazine, a hydrazone, a carboxyl group or salt thereof, a sulfonic acid group or salt thereof, a phosphoric acid group or salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, or —N($Q_1$)($Q_2$), where $Q_1$ and $Q_2$ are each independently selected from a hydrogen atom, a substituted or unsubstituted $C_1$-$C_{60}$ alkyl group, a substituted or unsubstituted $C_6$-$C_{30}$ aryl group, or a substituted or unsubstituted $C_2$-$C_{30}$ heteroaryl group, and two or more substituents of $R_5$ to $R_8$ may optionally bind to each other to form a ring; and n is 1 or 2.

2. The iridium complex of claim 1, wherein
$R_6$ is a hydrogen atom, a deuterium atom, a halogen, a hydroxyl group, a cyano group, a nitro group, or a halogen-substituted $C_1$-$C_{60}$ alkyl group.

3. The iridium complex of claim 1, wherein
$R_1$ to $R_4$, $R_5$, $R_7$, and $R_8$ are each independently a hydrogen atom or a deuterium atom.

4. The iridium complex of claim 1, wherein
the iridium complex of Formula 1 is represented by Formula 2 below:

Formula 2

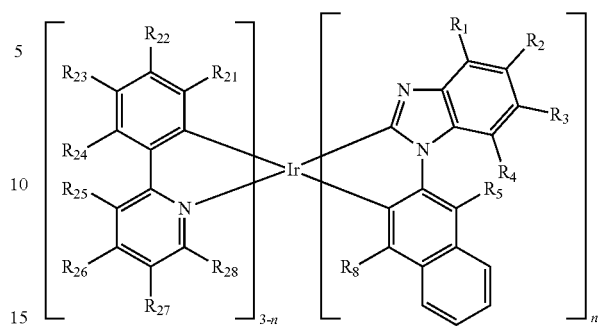

5. The iridium complex of claim 1, wherein
$R_{22}$ and $R_{24}$ are each independently a halogen.

6. The iridium complex of claim 5, wherein
$R_{22}$ and $R_{24}$ are each independently —F.

7. The iridium complex of claim 1, wherein
$R_{23}$ and $R_{26}$ are each independently selected from a hydrogen atom, a deuterium atom, a nitro group, a cyano group, a halogen-substituted $C_1$-$C_{60}$ alkyl group, an unsubstituted $C_1$-$C_{60}$ alkyl group, or N($Q_1$)($Q_2$) where $Q_1$ and $Q_2$ are each independently selected from a hydrogen atom, a substituted or unsubstituted $C_1$-$C_{60}$ alkyl group, a substituted or unsubstituted $C_6$-$C_{30}$ aryl group, or a substituted or unsubstituted $C_2$-$C_{30}$ heteroaryl group.

8. The iridium complex of claim 1, wherein
$R_{21}$, $R_{25}$, $R_{27}$, and $R_{28}$ are each independently a hydrogen atom or a deuterium atom.

9. The iridium complex of claim 1, wherein
the iridium complex of Formula 1 is any one of Compounds 1-18 below:

1

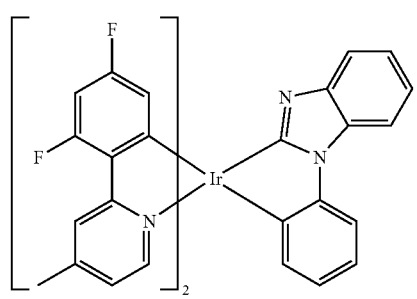

2

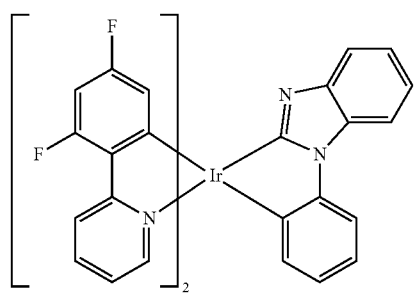

3
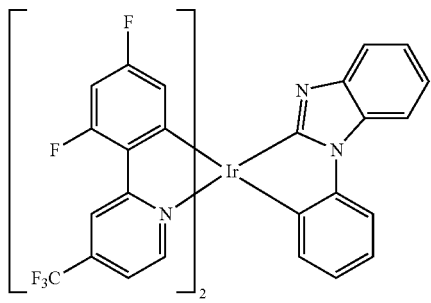
4
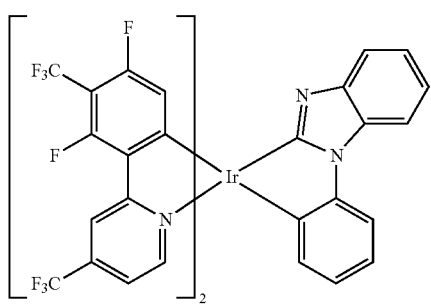
5
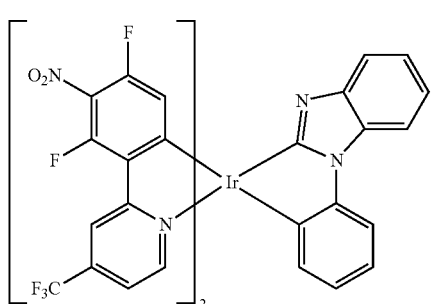
6
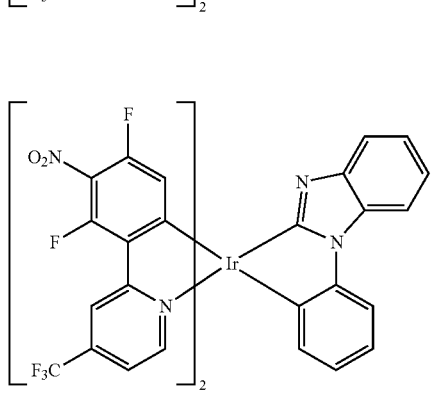
7
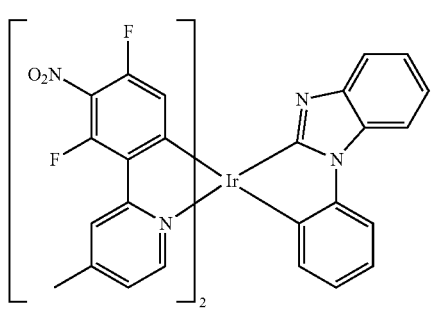
8
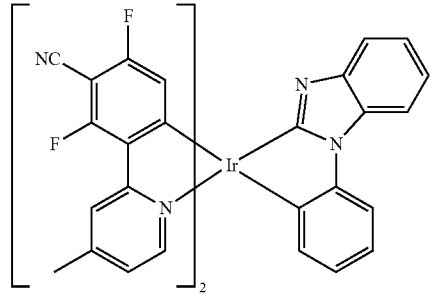
9
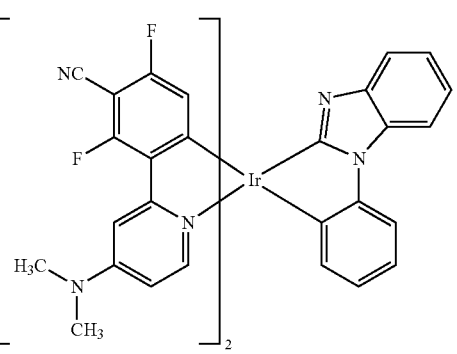
10
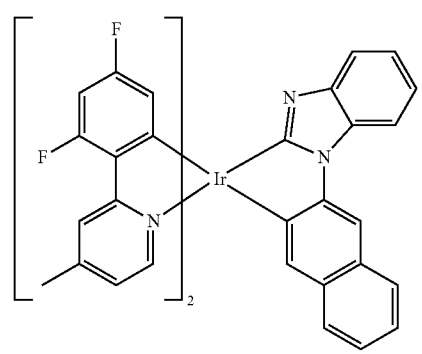
11
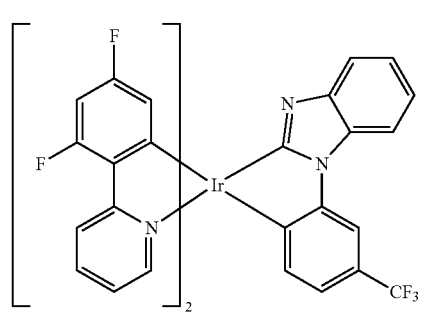
12
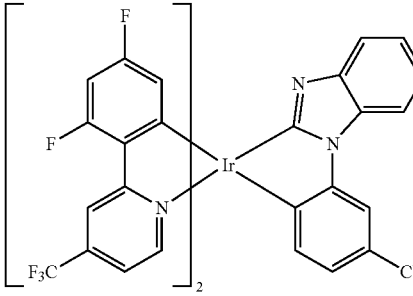

13

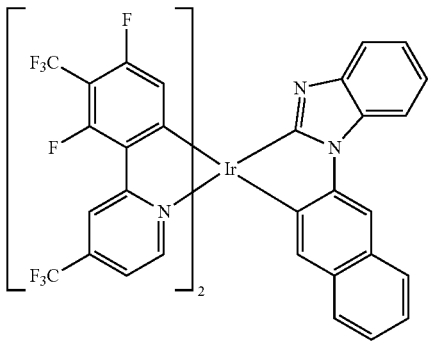

14

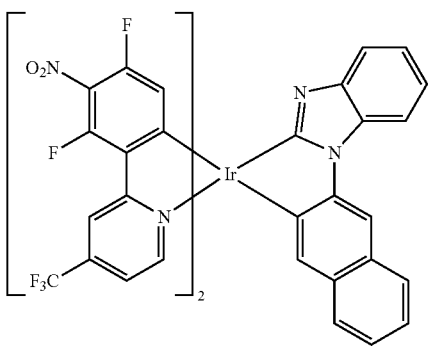

15

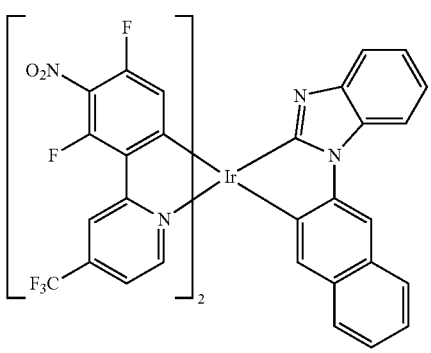

16

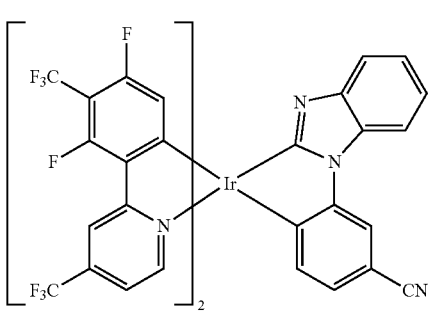

17

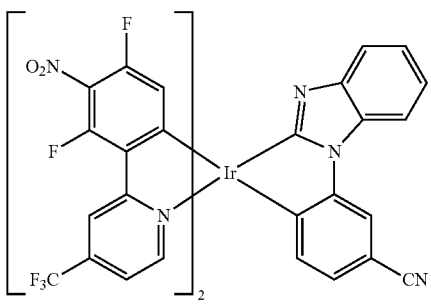

18

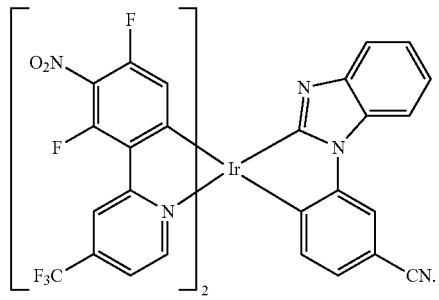

10. An organic light-emitting display device comprising:
a first electrode;
a second electrode; and
an organic layer between the first electrode and the second electrode, the organic layer comprising the iridium complex of claim 1.

11. The organic light-emitting device of claim 10, wherein the organic layer is an emission layer.

12. The organic light-emitting device of claim 10, wherein the organic layer is a green or blue phosphorescent emission layer, and the iridium complex is used as a phosphorescent dopant.

13. The organic light-emitting device of claim 10, wherein the organic layer comprises at least one of an emission layer, a hole injection layer, a hole transport layer, a functional layer having a hole injection capability and a hole transportation capability, an electron injection layer, an electron transport layer, or a functional layer having an electron injection capability and an electron transportation capability,
the emission layer comprises the iridium complex, and
the emission layer further comprises an anthracene-based compound, an arylamine-based compound, or a styryl-based compound.

14. The organic light-emitting device of claim 10, wherein the organic layer comprises at least one of an emission layer, a hole injection layer, a hole transport layer, or a functional layer having a hole injection capability and a hole transportation capability,
a green layer or a blue layer of the emission layer comprises the iridium complex, and
any one layer of a red layer and a white layer of the emission layer comprises a phosphorescent compound.

15. The organic light-emitting device of claim 14, wherein at least one of the hole injection layer, the hole transport layer, or the functional layer having a hole injection capability and a hole transportation capability comprises a charge-generation material.

16. The organic light-emitting device of claim 15, wherein the charge-generation material is a p-dopant.

17. The organic light-emitting device of claim 16, wherein the p-dopant is a quinone derivative, a metal oxide, or a cyano group-containing compound.

18. The organic light-emitting device of claim 10, wherein the organic layer comprises at least one of an emission layer, an electron injection layer, an electron transport layer, or a functional layer having an electron injection capability and an electron transportation capability,
the emission layer comprises the iridium complex, and
at least one of the electron injection layer, the electron transport layer, or the functional layer having an electron injection capability and an electron transportation capability comprises an electron transportation organic compound and a metal complex.

19. The organic light-emitting device of claim 10, wherein the organic layer is formed by wet chemistry and using the iridium complex.

20. A flat display apparatus comprising the organic light-emitting device of claim 10, wherein the first electrode of the organic light-emitting device is electrically connected to a source electrode or a drain electrode of a thin film transistor.

* * * * *